US010344301B2

(12) United States Patent
Ghadessy et al.

(10) Patent No.: US 10,344,301 B2
(45) Date of Patent: Jul. 9, 2019

(54) MUTANTS OF THE BACTERIOPHAGE LAMBDA INTEGRASE

(71) Applicant: AGENCY FOR SCIENCE, TECHNOLOGY AND RESEARCH, Singapore (SG)

(72) Inventors: Farid Ghadessy, Biopolis (SG); Jia Wei Siau, Singapore (SG); Peter Droge, Singapore (SG); Harshyaa Makhija, Singapore (SG); Shree Harsh Vijaya Chandra, Singapore (SG); Sabrina Peter, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 41 days.

(21) Appl. No.: 15/502,783

(22) PCT Filed: Aug. 11, 2015

(86) PCT No.: PCT/SG2015/050255
§ 371 (c)(1),
(2) Date: Feb. 8, 2017

(87) PCT Pub. No.: WO2016/022075
PCT Pub. Date: Feb. 11, 2016

(65) Prior Publication Data

US 2017/0327847 A1 Nov. 16, 2017

(30) Foreign Application Priority Data

Aug. 8, 2014 (GB) .................................. 1414130.3

(51) Int. Cl.

| | |
|---|---|
| ***C12N 9/12*** | (2006.01) |
| ***C12N 9/22*** | (2006.01) |
| ***C12N 1/15*** | (2006.01) |
| ***C12N 1/21*** | (2006.01) |
| ***C12P 19/34*** | (2006.01) |
| ***C12N 15/90*** | (2006.01) |

(52) U.S. Cl.
CPC ......... *C12N 15/907* (2013.01); *C12N 9/1241* (2013.01); *C12N 9/22* (2013.01); *C12N 15/90* (2013.01); *C12N 2795/10322* (2013.01)

(58) Field of Classification Search
None
See application file for complete search history.

(56) References Cited

U.S. PATENT DOCUMENTS

2013/0017578 A1 1/2013 Ghadessy et al.

FOREIGN PATENT DOCUMENTS

CA 2522166 12/2002

OTHER PUBLICATIONS

UniProt Database Accession No. V0VKX3, Jan. 2014, 1 page (Year: 2014).*
PCT Notification of Transmittal of the International Search Report and the Written Opinion of the International Searching Authority, or the Declaration for PCT Counterpart Application No. PCT/SG2015/050255, 1 pg., (dated Aug. 11, 2015).
Tay, et al., "Selection of bacteriophage λ integrases with altered recombination specificity by in vitro compartmentalization", Nucleic Acids Research, vol. 38, No. 4, Dec. 4, 2009, E25.
Extended European Search Report for European application No. 15829802.6, dated Nov. 28, 2017.
Siau, et al., "Directed evolution of λ integrase activity and specificity by genetic depression", Protein Engineering, Design and Selection, vol. 28, No. 7, Mar. 18, 2015, 211-220.
PCT International Search Report, 5 pgs., (dated Nov. 6, 2015).
Written Opinion of the International Searching Authority, 6 pgs., (dated Nov. 6, 2015).
Laszlo Dorgai, et al., "Identifying Determinants of Recombination Specificity: Construction and Characterization of Mutant Bacteriophage Integrases," J. Mol. Biol., vol. 252, pp. 178-189 (1995).

* cited by examiner

*Primary Examiner* — David Steadman
(74) *Attorney, Agent, or Firm* — Womble Bond Dickinson (US) LLP

(57) ABSTRACT

The present invention refers to lambda integrases comprising at least one amino acid mutation at positions 43, 319 and 336 of the lambda integrase as set forth in SEQ ID NO: 1. The invention further refers to nucleic acid molecules comprising the nucleotide sequence encoding the mutant lambda integrase and to host cells containing these nucleic acid molecules. The invention also refers to methods of recombining a nucleic acid of interest into a target nucleic acid in the presence of the mutant lambda integrase and sequence specific recombination kits.

13 Claims, 10 Drawing Sheets

Specification includes a Sequence Listing.

FIG 1

| | Core-binding sequence | | | | | | | Overlap sequence | | | | | | | Core-binding sequence | | | | | | | |
|---|---|---|---|---|---|---|---|---|---|---|---|---|---|---|---|---|---|---|---|---|---|---|
| *att*B | C | T | G | C | T | T | T | T | T | T | A | T | A | C | T | A | A | C | T | T | G | (SEQ ID No. :5) |
| *att*H | C | T | G | C | T | T | T | C | T | T | A | T | A | C | C | A | A | G | T | G | G | (SEQ ID No. :7) |
| *att*H4X | A | C | G | C | T | T | T | A | T | T | T | C | A | T | T | A | A | G | T | T | G | (SEQ ID No. :31) |

| | | | | | | | | | | | | | | | | | | | | | | |
|---|---|---|---|---|---|---|---|---|---|---|---|---|---|---|---|---|---|---|---|---|---|---|
| *att*P | C | A | G | C | T | T | T | T | T | T | A | T | A | C | T | A | A | G | T | T | G | (SEQ ID No. :6) |
| *att*PH | C | A | G | C | T | T | T | C | T | T | A | T | A | C | C | A | A | G | T | G | G | (SEQ ID No. :8) |
| *att*P4X | C | A | G | C | T | T | T | A | T | T | T | C | A | T | T | A | A | G | T | T | G | (SEQ ID No. :9) |

FIGS 3A-B
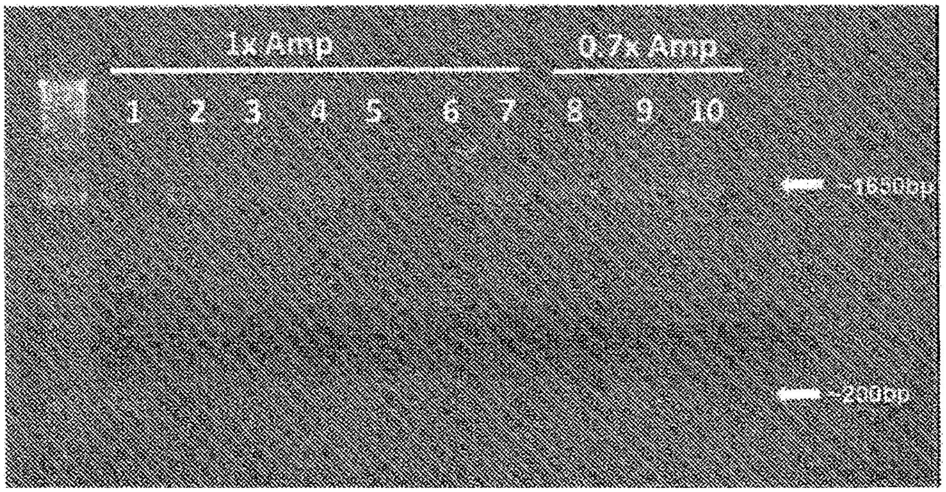
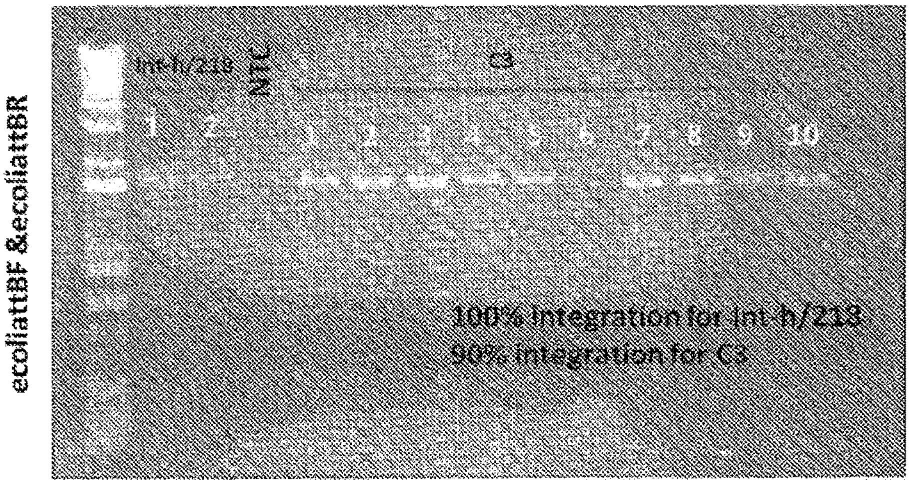

FIG 3C tgaatccgttgaagcCTGCTTTTTTATACTAAGTTGGCATTATAAAAAAGCATTGCTTA
TCAATTTGTTGCAACGAACAGGTCACTATCAGTCAAAATAAAATCATTATTTGA
TTTCCCGGTGATGTTCAGGTGGCACTTTTCGGGGAAATGTGCGCGGAACCCCT
ATTTGTTTATTTTTCTAAATACATTCAAATATGTATCCGCTCATGAGACAATAACC
CTGATAAATGCTTCAATAATATTGAAAAAGGAAGAGTATGAGTATTCAACATTTC
CGTGTCGCCCTTATTCCCTTTTTTGCGGCATTTTGCCTTCCTGTTTTTGCTCACC
CAGAAACGCTGGTGAAAGTAAAAGATGCTGAAGATCAGTTGGGTGCACGAGT
GGGTTACATCGAACTGGATCTCAACAGCGGTAAGATCCTTGAGAGTTTTCGCC
CCGAAGAACGTTTTCCAATGATGAGCACTTTTAAAGTTCTGCTATGTGGCGCG
GTATTATCCCGTATTGACGCCGGGCAAGAGCAACTCGGTCGCCGCATACACT
ATTCTCAGAATGACTTGGTTGAGTACTCACCAGTCACAGAAAAGCATCTTACG
GATGGCATGACAGTAAGAGAATTATGCAGTGCTGCCATAACCATGAGTGATA
ACACTGCGGCCAACTTACTTCTGACAACGATCGGAGGACCGAAGGAGCTAAC
CGCTTTTTTGCACAACATGGGGGATCATGTAACTCGCCTTGATCGTTGGGAAC
CGGAGCTGAATGAAGCCATACCAAACGACGAGCGTGACACCACGATGCCTG
CAGCAATGGCAACAACGTTGCGCAAACTATTAACTGGCGAACTACTTACTCTA
GCTTCCCGGCAACAATTAATAGACTGGATGGAGGCGGATAAAGTTGCAGGAC
CACTTCTGCGCTCGGCCCTTCCGGCTGGCTGGTTTATTGCTGATAAATCTGGA
GCCGGTGAGCGTGGGTCTCGCGGTATCATTGCAGCACTGGGGCCAGATGGTA
AGCCCTCCCGTATCGTAGTTATCTACACGACGGGGAGTCAGGCAACTATGGA
TGAACGAAATAGACAGATCGCTGAGATAGGTGCCTCACTGATTAAGCATTGGT
AACTGTCAGACCAAGTTTACTCATATATACTTTAGATTGATTTAAAACTTCATTTT
TAATTTAAAAGGATCTAGGTGAAGATCCTTTTTGATAATCTCATGACCAAAATCC
CTTAACGTGAGTTTTCGTTCCACTGAGCGTCAGACCCCGTAGAAAAGATCAAAG
GATCTTCTTGAGATCCTTTTTTTCTGCGCGTAATCTGCTGCTTGCAAACAAAAAA
ACCACCGCTACCAGCGGTGGTTTGTTTGCCGGATCAAGAGCTACCAACTCTTTT
CCGAAGGTAACTGGCTTCAGCAGAGCGCAGATACCAAATACTGTCCTTCTAGTG
TAGGAATTCCACAGAATTCCGTCTGTTACAGGTCACTAATACCATCTAAGTAGT
TGATTCATAGTGACTGCATATATTGTGTTTTACAGTATTATGTAGTCTGTTTTTT
ATGCAAAATCTAATTTAATATATTGATATTTATATCATTTTACGTTTCTCGTTCA
GCTTTTTTATACTAACTTGagcgaaacgggaaggtaaaaagacat (SEQ ID No. :32)

FIGS 5A-B
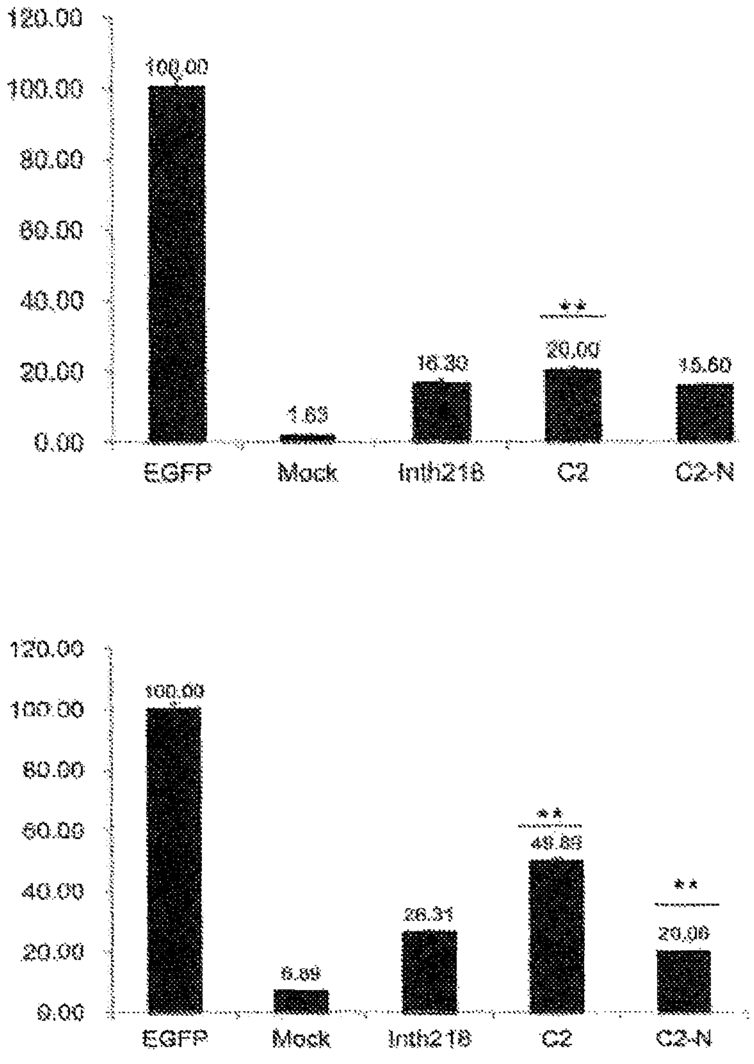

FIGS 5C-D
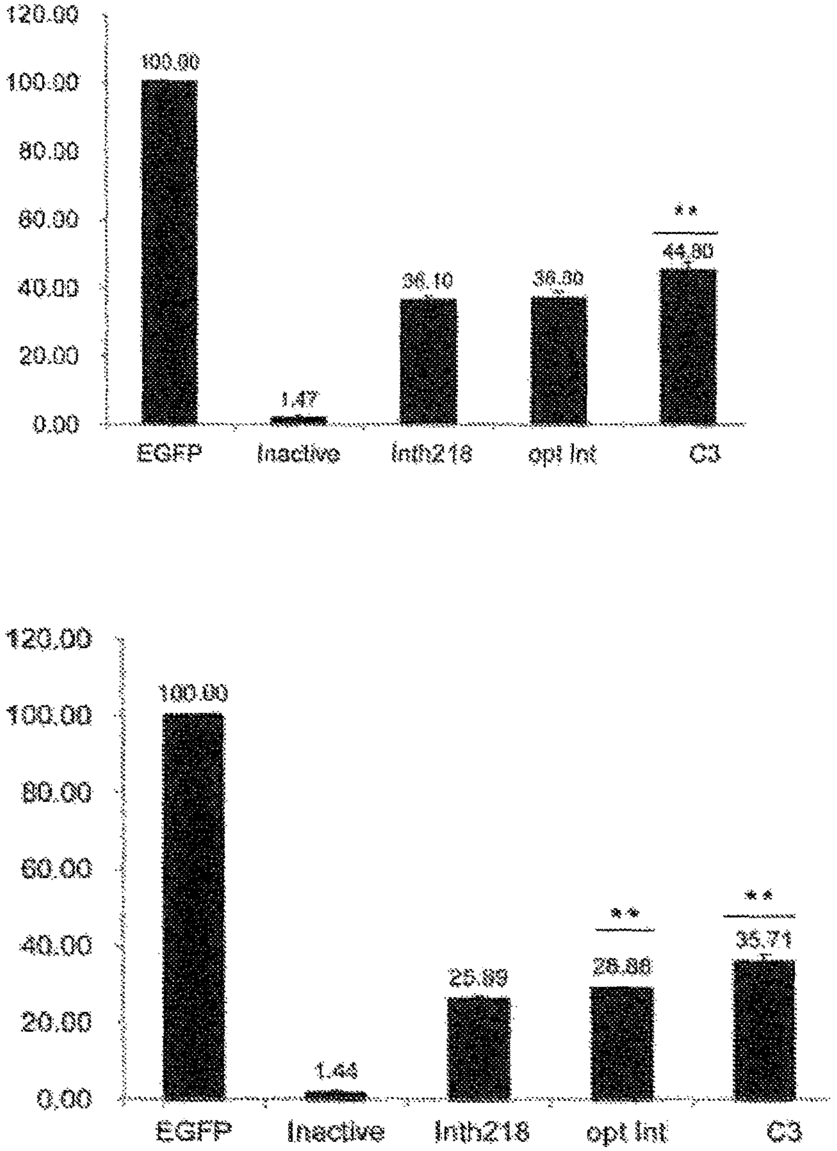

FIG 6B clone 3
ctttatgacccagtcatcgttggtttggtcttttcacatagtcccatgtttcttggagattt
tgttcattccttctcattcttttttctctaatcttgtcctc*ATGCTTTATTTCATTAAGTTG*
*GCATTATAAAAAAGCATTGCTTATCAATTTGTTGCAACGAACAGGTCACTATCAGTCAAAAT*
*ACAATCATTATTTGATTTCAATTTTGTCCCACTCCCTCCCG*AATTCTACCGGGTAGGGGAGG
CGCTTTTCCCAAGGCAGTCTGGAGCATGCGCTTTAGCAGCCCCGCTGGGCACTTGGCGCTAC
ACAAGTGGCCTCTGGCCTCGCACACATTCCACATCCACCGGTAGGCGCCAACCGGCTCCGTT
CTTTGGTGGCCCCTTCGCGCCACCTTCTACTCCTCCCCTAGTCAGGAAGTTCCCCCCCGCCC
CGCAGCTCGCGTCGTGCAGGACGTGACAAATGGAAGTAGCACGTCTCACTAGTCTCGTGCAG
ATGGACAGCACCGCTGAGCAATGGAAGCGGGTAGGCCTTTGGGGCAGCGGCCAATAGCAGCT
Targeted locus: Chromosome 19 (35188923-35188943) (SEQ ID No. :33)

clone 19
gattcggtaaccaatcaaatgtaagcttggtcttttcacataatcccatatttttggaggc
tttgttcatttcttttcattcttttttctctaatctgtcttc*ATGCTTTATTTCATTAAGTT*
*GGCATTATAAAAAGCATTGCTTATCAATTTGTTGCAACGAACAGGTCACTATCAGTCAAAA*
*TACAATCATTATTTGATTTCAATTTTGTCCCACTCCCTCCCG*AATTCTACCGGGTAGGGGAG
GCGCTTTTCCCAAGGCAGTCTGGAGCATGCGCTTTAGCAGCCCCGCTGGGCACTTGGCGCTA
CACAAGTGGCCTCTGGCCTCGCACACATTCCACATCCACCGGTAGGCGCCAACCGGCTCCGT
TCTTTGGTGGCCCCTTCGCGCCACCTTCTACTCCTCCCCTAGTCAGGAAGTTCCCCCCCGCC
CCGCAGCTCGCGTCGTGCAGGACGTGACAAATGGAAGTAGCACGTCTCACTAGTCTCGTGCA
GATGGACAGCACCGCTGAGCAATGGAAGCGGGTAGGCCTTTGGGGCAGCGGCCAATAGCAGC
Targeted locus: Chromosome 2 (153753805-153753825)(SEQ ID No. :34)

SEQUENCE LISTING

```
<160> NUMBER OF SEQ ID NOS: 34

<210> SEQ ID NO 1
<211> LENGTH: 356
<212> TYPE: PRT
<213> ORGANISM: Bacteriophage lambda

<400> SEQUENCE: 1

Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Lys Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
```

```
        195                 200                 205

Thr Gly Gln Arg Val Gly Asp Leu Cys Lys Met Lys Trp Ser Asp Ile
    210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
    290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335

Thr Met Ala Ser Gln Tyr Arg Asp Asp Arg Gly Arg Glu Trp Asp Lys
            340                 345                 350

Ile Glu Ile Lys
        355


<210> SEQ ID NO 2
<211> LENGTH: 356
<212> TYPE: PRT
<213> ORGANISM: Artificial Sequence
<220> FEATURE:
<223> OTHER INFORMATION: C2 lambda integrase mutant

<400> SEQUENCE: 2

Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Lys Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
```

```
        195                 200                 205

Thr Gly Gln Arg Val Gly Asp Leu Cys Lys Met Lys Trp Ser Asp Ile
    210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
    290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Val
                325                 330                 335

Thr Met Ala Ser Gln Tyr Arg Asp Asp Arg Gly Arg Glu Trp Asp Lys
            340                 345                 350

Ile Glu Ile Lys
        355


<210> SEQ ID NO 3
<211> LENGTH: 356
<212> TYPE: PRT
<213> ORGANISM: Artificial Sequence
<220> FEATURE:
<223> OTHER INFORMATION: C3 lambda integrase mutant

<400> SEQUENCE: 3

Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Phe Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Lys Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
```

```
        195                 200                 205

Thr Gly Gln Arg Val Gly Asp Leu Cys Lys Met Lys Trp Ser Asp Ile
    210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
    290                 295                 300

Pro Thr Phe His Glu Leu Arg Ser Leu Ser Ala Arg Leu Tyr Gly Lys
305                 310                 315                 320

Gln Ile Ser Asp Lys Phe Ala Gln His Leu Leu Gly His Lys Ser Val
                325                 330                 335

Thr Met Ala Ser Gln Tyr Arg Asp Asp Arg Gly Arg Glu Trp Asp Lys
            340                 345                 350

Ile Glu Ile Lys
        355


<210> SEQ ID NO 4
<211> LENGTH: 1071
<212> TYPE: DNA
<213> ORGANISM: Bacteriophage lambda

<400> SEQUENCE: 4

atgggaagaa ggcgaagtca tgagcgccgg gatttacccc ctaaccttta tataagaaac      60

aatggatatt actgctacag ggacccaagg acgggtaaag agtttggatt aggcagagac     120

aggcgaatcg caatcactga agctatacag gccaacattg agttattttc aggacacaaa     180

cacaagcctc tgacagcgag aatcaacagt gataattccg ttacgttaca ttcatggctt     240

gatcgctacg aaaaaatcct ggccagcaga ggaatcaagc agaagacact cataaattac     300

atgagcaaaa ttaaagcaat aaggaggggt ctgcctgatg ctccacttga agacatcacc     360

acaaaagaaa ttgcggcaat gctcaatgga tacatagacg agggcaaggc ggcgtcagcc     420

aagttaatca gatcaacact gagcgatgca ttccgagagg caatagctga aggccatata     480

acaacaaacc atgtcgctgc cactcgcgca gcaaaatcaa aggtaaggag atcaagactt     540

acggctgacg aatacctgaa aatttatcaa gcagcagaat catcaccatg ttggctcaga     600

cttgcaatgg aactggctgt tgttaccggg caacgagttg gtgatttatg caaaatgaag     660

tggtctgata tcgtagatgg atatctttat gtcgagcaaa gcaaaacagg cgtaaaaatt     720

gccatcccaa cagcattgca tattgatgct ctcggaatat caatgaagga aacacttgat     780

aaatgcaaag agattcttgg cggagaaacc ataattgcat ctactcgtcg cgaaccgctt     840

tcatccggca cagtatcaag gtattttatg cgcgcacgaa aagcatcagg tctttccttc     900

gaaggggatc cgcctacctt tcacgagttg cgcagtttgt ctgcaagact ctatgagaag     960

cagataagcg ataagtttgc tcaacatctt ctcgggcata agtcggacac catggcatca    1020

cagtatcgtg atgacagagg cagggagtgg gacaaaattg aaatcaaata a             1071


<210> SEQ ID NO 5
<211> LENGTH: 21
```

```
<212> TYPE: DNA
<213> ORGANISM: Artificial Sequence
<220> FEATURE:
<223> OTHER INFORMATION: attB attachment site

<400> SEQUENCE: 5

ctgctttttt atactaactt g                                              21

<210> SEQ ID NO 6
<211> LENGTH: 21
<212> TYPE: DNA
<213> ORGANISM: Artificial Sequence
<220> FEATURE:
<223> OTHER INFORMATION: attP attachment site

<400> SEQUENCE: 6

cagctttttt atactaagtt g                                              21

<210> SEQ ID NO 7
<211> LENGTH: 21
<212> TYPE: DNA
<213> ORGANISM: Artificial Sequence
<220> FEATURE:
<223> OTHER INFORMATION: attH attachment site

<400> SEQUENCE: 7

ctgctttctt ataccaagtg g                                              21

<210> SEQ ID NO 8
<211> LENGTH: 21
<212> TYPE: DNA
<213> ORGANISM: Artificial Sequence
<220> FEATURE:
<223> OTHER INFORMATION: attPH attachment site

<400> SEQUENCE: 8

cagctttctt ataccaagtt g                                              21

<210> SEQ ID NO 9
<211> LENGTH: 21
<212> TYPE: DNA
<213> ORGANISM: Artificial Sequence
<220> FEATURE:
<223> OTHER INFORMATION: attP4X attachment site

<400> SEQUENCE: 9

cagctttatt tcattaagtt g                                              21

<210> SEQ ID NO 10
<211> LENGTH: 19
<212> TYPE: DNA
<213> ORGANISM: Artificial Sequence
<220> FEATURE:
<223> OTHER INFORMATION: petF2 Primer

<400> SEQUENCE: 10

catcggtgat gtcggcgat                                                 19

<210> SEQ ID NO 11
<211> LENGTH: 24
<212> TYPE: DNA
<213> ORGANISM: Artificial Sequence
<220> FEATURE:
<223> OTHER INFORMATION: petR Primer

<400> SEQUENCE: 11
```

-continued cggatatagt tcctcctttc agca 24

<210> SEQ ID NO 12
<211> LENGTH: 38
<212> TYPE: DNA
<213> ORGANISM: Artificial Sequence
<220> FEATURE:
<223> OTHER INFORMATION: attP-F Primer

<400> SEQUENCE: 12
cacagaattc cgtctgttac aggtcactaa taccatct 38

<210> SEQ ID NO 13
<211> LENGTH: 52
<212> TYPE: DNA
<213> ORGANISM: Artificial Sequence
<220> FEATURE:
<223> OTHER INFORMATION: attPSOE-R Primer

<400> SEQUENCE: 13
acatttcccc gaaaagtgcc acctgaacat caccgggaaa tcaaataatg at 52

<210> SEQ ID NO 14
<211> LENGTH: 27
<212> TYPE: DNA
<213> ORGANISM: Artificial Sequence
<220> FEATURE:
<223> OTHER INFORMATION: TEM1prom-F Primer

<400> SEQUENCE: 14
ttcaggtggc acttttcggg gaaatgt 27

<210> SEQ ID NO 15
<211> LENGTH: 41
<212> TYPE: DNA
<213> ORGANISM: Artificial Sequence
<220> FEATURE:
<223> OTHER INFORMATION: TEM1prom-R Primer

<400> SEQUENCE: 15
tgtggaattc ctacactaga aggacagtat ttggtatctg c 41

<210> SEQ ID NO 16
<211> LENGTH: 24
<212> TYPE: DNA
<213> ORGANISM: Artificial Sequence
<220> FEATURE:
<223> OTHER INFORMATION: EcoliAttB-F Primer

<400> SEQUENCE: 16
ctgaaaatgt gttcacaggt tgct 24

<210> SEQ ID NO 17
<211> LENGTH: 21
<212> TYPE: DNA
<213> ORGANISM: Artificial Sequence
<220> FEATURE:
<223> OTHER INFORMATION: EcoliattB-R Primer

<400> SEQUENCE: 17
gcaatgccat ctggtatcac t 21

<210> SEQ ID NO 18
<211> LENGTH: 1071
<212> TYPE: DNA
<213> ORGANISM: Artificial Sequence
<220> FEATURE:
<223> OTHER INFORMATION: C2 mutant gene

<400> SEQUENCE: 18

| | |
|---|---|
| atgggaagaa ggcgaagtca tgagcgccgg gatttacccc ctaaccttta tataagaaac | 60 |
| aatggatatt actgctacag ggacccaagg acgggtaaag agtttggatt aggcagagac | 120 |
| aggcgaatcg caatcactga agctatacag gccaacattg agttattttc aggacacaaa | 180 |
| cacaagcctc tgacagcgag aatcaacagt gataattccg ttacgttaca ttcatggctt | 240 |
| gatcgctacg aaaaaatcct ggccagcaga ggaatcaagc agaagacact cataaattac | 300 |
| atgagcaaaa ttaaagcaat aaggaggggt ctgcctgatg ctccacttga agacatcacc | 360 |
| acaaaagaaa ttgcggcaat gctcaatgga tacatagacg agggcaaggc ggcgtcagcc | 420 |
| aagttaatca gatcaacgct gagcgatgca ttccgagagg caatagctga aggccatata | 480 |
| acaacaaacc atgtcgctgc cactcgcgca gcaaagtcaa aggtaaggag atcaagactt | 540 |
| acggctgacg aatacctgaa aatttatcaa gcagcagaat catcaccatg ttggctcaga | 600 |
| cttgcaatgg aactggctgt tgttaccggg caacgagttg gtgacttgtg caaaatgaag | 660 |
| tggtctgata tcgtagatgg atatctttat gtcgagcaaa gcaaaacagg cgtaaaaatt | 720 |
| gccatcccaa cagcattgca tattgatgct ctcggaatat caatgaagga aacacttgat | 780 |
| aaatgcaaag agattcttgg cggagaaacc ataattgcat ctactcgtcg cgaaccgctt | 840 |
| tcatccggca cagtatcaag gtattttatg cgcgcacgaa aagcatcagg tctttccttc | 900 |
| gaagggggatc cgcctacctt tcacgagttg cgcagtttgt ctgcaagact ctatgagaag | 960 |
| cagataagcg ataagtttgc tcaacatctt ctcgggcata agtcggtcac catggcatca | 1020 |
| cagtatcgtg atgacagagg cagggagtgg gacaaaattg aaatcaaata a | 1071 |

<210> SEQ ID NO 19
<211> LENGTH: 1071
<212> TYPE: DNA
<213> ORGANISM: Artificial Sequence
<220> FEATURE:
<223> OTHER INFORMATION: C3 mutant gene

<400> SEQUENCE: 19

| | |
|---|---|
| atgggaagaa ggcgaagtca tgagcgccgg gatttacccc ctaaccttta tataagaaac | 60 |
| aatggatatt actgctacag ggacccaagg acgggtaaag agtttggatt aggcagagac | 120 |
| aggcgattcg caatcactga agctatacag gccaacattg agttattttc aggacacaaa | 180 |
| cacaagcctc tgacagcgag aatcaacagt gataattccg ttacgttaca ttcatggctt | 240 |
| gatcgctacg aaaaaatcct ggccagcaga ggaatcaagc agaagacact cataaattac | 300 |
| atgagcaaaa ttaaagcaat aaggaggggt ctgcctgatg ctccacttga agacatcacc | 360 |
| acaaaagaaa ttgcggcaat gctcaatgga tacatagacg agggcaaggc ggcgtcagcc | 420 |
| aagttaatca gatcaacgct gagcgatgca ttccgagagg caatagctga aggccatata | 480 |
| acaacaaacc atgtcgctgc cactcgcgcg gcaaagtcaa aggtaaggag atcaagactt | 540 |
| acggctgacg aatacctgaa aatttatcaa gcagcagaat catcaccatg ttggctcaga | 600 |
| cttgcaatgg aactggctgt tgttaccggg caacgagttg gtgacttgtg caaaatgaag | 660 |
| tggtctgata tcgtagatgg atatctttat gtcgagcaaa gcaaaacagg cgtaaaaatt | 720 |
| gccatcccaa cagcattgca tattgatgct ctcggaatat caatgaagga aacacttgat | 780 |
| aaatgcaaag agattcttgg cggagaaacc ataattgcat ctactcgtcg cgaaccgctc | 840 |

-continued tcatccggca cagtatcaag gtattttatg cgcgcacgaa aagcatcagg tctttccttc 900
gaaggggatc cgcctacctt tcacgagttg cgcagtttgt ctgcaagact ctatgggaag 960
cagataagcg ataagtttgc tcaacatctt ctcgggcata agtcggtcac catggcatca 1020
cagtatcgtg atgacagagg cagggagtgg gacaaaattg aaatcaaata a 1071

<210> SEQ ID NO 20
<211> LENGTH: 1481
<212> TYPE: DNA
<213> ORGANISM: Artificial Sequence
<220> FEATURE:
<223> OTHER INFORMATION: C3 mutant minicircle DNA

<400> SEQUENCE: 20
catcggtgat gtcggcgata taggcgccag caaccgcacc tgtggcgccg gtgatgccgg 60
ccacgatgcg tccggcgtag aggatcgaga tctcgatccc gcgaaattaa tacgactcac 120
tataggggaa ttgtgagcgg ataacaattc ccctctagaa ataattttgt ttaactttaa 180
gaaggagata tacatatggg aagaaggcga agtcatgagc gccgggattt accccctaac 240
ctttatataa gaaacaatgg atattactgc tacagggacc caaggacggg taaagagttt 300
ggattaggca gagacaggcg attcgcaatc actgaagcta tacaggccaa cattgagtta 360
ttttcaggac acaaacacaa gcctctgaca gcgagaatca acagtgataa ttccgttacg 420
ttacattcat ggcttgatcg ctacgaaaaa atcctggcca gcagaggaat caagcagaag 480
acactcataa attacatgag caaaattaaa gcaataagga ggggtctgcc tgatgctcca 540
cttgaagaca tcaccacaaa agaaattgcg gcaatgctca atggatacat agacgagggc 600
aaggcggcgt cagccaagtt aatcagatca acgctgagcg atgcattccg agaggcaata 660
gctgaaggcc atataacaac aaaccatgtc gctgccactc gcgcggcaaa gtcaaaggta 720
aggagatcaa gacttacggc tgacgaatac ctgaaaattt atcaagcagc agaatcatca 780
ccatgttggc tcagacttgc aatggaactg gctgttgtta ccgggcaacg agttggtgac 840
ttgtgcaaaa tgaagtggtc tgatatcgta gatggatatc tttatgtcga gcaaagcaaa 900
acaggcgtaa aaattgccat cccaacagca ttgcatattg atgctctcgg aatatcaatg 960
aaggaaacac ttgataaatg caaagagatt cttggcggag aaaccataat tgcatctact 1020
cgtcgcgaac cgctctcatc cggcacagta tcaaggtatt ttatgcgcgc acgaaaagca 1080
tcaggtcttt ccttcgaagg ggatccgcct acctttcacg agttgcgcag tttgtctgca 1140
agactctatg ggaagcagat aagcgataag tttgctcaac atcttctcgg gcataagtcg 1200
gtcaccatgg catcacagta tcgtgatgac agaggcaggg agtgggacaa aattgaaatc 1260
aaacatcatc accatcacca ctaatgagaa ttcgagctcc gtcgacaagc ttgcggccgc 1320
actcgagcac caccaccacc accactgaga tccggctgct aacaaagccc gaaaggaagc 1380
tgagttggct gctgccaccg ctgagcaata actagcataa ccccttgggg cctctaaacg 1440
ggtcttgagg ggttttttgc tgaaaggagg aactatatcc g 1481

<210> SEQ ID NO 21
<211> LENGTH: 1599
<212> TYPE: DNA
<213> ORGANISM: Artificial Sequence
<220> FEATURE:
<223> OTHER INFORMATION: attP-TEM1 minicircle

<400> SEQUENCE: 21
cacagaattc cgtctgttac aggtcactaa taccatctaa gtagttgatt catagtgact 60

```
gcatatattg tgttttacag tattatgtag tctgtttttt atgcaaaatc taatttaata    120

tattgatatt tatatcattt tacgtttctc gttcagcttt tttatactaa gttggcatta    180

taaaaaagca ttgcttatca atttgttgca acgaacaggt cactatcagt caaaataaaa    240

tcattatttg atttcccggt gatgttcagg tggcactttt cggggaaatg tgcgcggaac    300

ccctatttgt ttatttttct aaatacattc aaatatgtat ccgctcatga gacaataacc    360

ctgataaatg cttcaataat attgaaaaag gaagagtatg agtattcaac atttccgtgt    420

cgcccttatt cccttttttg cggcattttg ccttcctgtt tttgctcacc cagaaacgct    480

ggtgaaagta aaagatgctg aagatcagtt gggtgcacga gtgggttaca tcgaactgga    540

tctcaacagc ggtaagatcc ttgagagttt tcgccccgaa gaacgttttc caatgatgag    600

cacttttaaa gttctgctat gtggcgcggt attatcccgt attgacgccg ggcaagagca    660

actcggtcgc cgcatacact attctcagaa tgacttggtt gagtactcac cagtcacaga    720

aaagcatctt acggatggca tgacagtaag agaattatgc agtgctgcca taaccatgag    780

tgataacact gcggccaact tacttctgac aacgatcgga ggaccgaagg agctaaccgc    840

ttttttgcac aacatggggg atcatgtaac tcgccttgat cgttgggaac cggagctgaa    900

tgaagccata ccaaacgacg agcgtgacac cacgatgcct gcagcaatgg caacaacgtt    960

gcgcaaacta ttaactggcg aactacttac tctagcttcc cggcaacaat taatagactg   1020

gatggaggcg gataaagttg caggaccact tctgcgctcg gcccttccgg ctggctggtt   1080

tattgctgat aaatctggag ccggtgagcg tgggtctcgc ggtatcattg cagcactggg   1140

gccagatggt aagccctccc gtatcgtagt tatctacacg acggggagtc aggcaactat   1200

ggatgaacga aatagacaga tcgctgagat aggtgcctca ctgattaagc attggtaact   1260

gtcagaccaa gtttactcat atatacttta gattgattta aaacttcatt tttaatttaa   1320

aaggatctag gtgaagatcc tttttgataa tctcatgacc aaaatccctt aacgtgagtt   1380

ttcgttccac tgagcgtcag accccgtaga aaagatcaaa ggatcttctt gagatccttt   1440

ttttctgcgc gtaatctgct gcttgcaaac aaaaaaacca ccgctaccag cggtggtttg   1500

tttgccggat caagagctac caactctttt tccgaaggta actggcttca gcagagcgca   1560

gataccaaat actgtccttc tagtgtagcc gtagttagg                         1599


<210> SEQ ID NO 22
<211> LENGTH: 21
<212> TYPE: DNA
<213> ORGANISM: Artificial Sequence
<220> FEATURE:
<223> OTHER INFORMATION: HOP sequence

<400> SEQUENCE: 22

atgctttatt tcattaagtt g                                               21


<210> SEQ ID NO 23
<211> LENGTH: 103
<212> TYPE: DNA
<213> ORGANISM: Artificial Sequence
<220> FEATURE:
<223> OTHER INFORMATION: attL attachment site

<400> SEQUENCE: 23

gcattataaa aaagcattgc ttatcaattt gttgcaacga acaggtcact atcagtcaaa     60

atacaatcat tatttgattt caattttgtc ccactccctc ccg                      103
```

-continued

<210> SEQ ID NO 24
<211> LENGTH: 331
<212> TYPE: DNA
<213> ORGANISM: Artificial Sequence
<220> FEATURE:
<223> OTHER INFORMATION: PGK Promoter

<400> SEQUENCE: 24
aattctaccg ggtaggggag gcgcttttcc caaggcagtc tggagcatgc gctttagcag 60
ccccgctggg cacttggcgc tacacaagtg gcctctggcc tcgcacacat tccacatcca 120
ccggtaggcg ccaaccggct ccgttctttg gtggcccctt cgcgccacct tctactcctc 180
ccctagtcag gaagttcccc cccgccccgc agctcgcgtc gtgcaggacg tgacaaatgg 240
aagtagcacg tctcactagt ctcgtgcaga tggacagcac cgctgagcaa tggaagcggg 300
taggcctttg gggcagcggc caatagcagc t 331

<210> SEQ ID NO 25
<211> LENGTH: 25
<212> TYPE: DNA
<213> ORGANISM: Artificial Sequence
<220> FEATURE:
<223> OTHER INFORMATION: HOP' attH4X_F1 Primer

<400> SEQUENCE: 25
gagtgttttc caacttggtt ccatt 25

<210> SEQ ID NO 26
<211> LENGTH: 22
<212> TYPE: DNA
<213> ORGANISM: Artificial Sequence
<220> FEATURE:
<223> OTHER INFORMATION: PuroRev24 Primer

<400> SEQUENCE: 26
caccgtgggc ttgtactcgg tc 22

<210> SEQ ID NO 27
<211> LENGTH: 21
<212> TYPE: DNA
<213> ORGANISM: Artificial Sequence
<220> FEATURE:
<223> OTHER INFORMATION: pLIR-F1 Primer

<400> SEQUENCE: 27
ctgcatcgat tcagctagct g 21

<210> SEQ ID NO 28
<211> LENGTH: 22
<212> TYPE: DNA
<213> ORGANISM: Artificial Sequence
<220> FEATURE:
<223> OTHER INFORMATION: pLIR-R1 Primer

<400> SEQUENCE: 28
ctgatagtga cctgttcgtt gc 22

<210> SEQ ID NO 29
<211> LENGTH: 4906
<212> TYPE: DNA
<213> ORGANISM: Artificial Sequence
<220> FEATURE:
<223> OTHER INFORMATION: pPGKssPuro-attP4X (targeting vector)

<400> SEQUENCE: 29

-continued

```
gaattcctct gttacaggtc actaatacca tctaagtagt tgattcatag tgactgcata     60
tgttgtgttt tacagtatta tgtagtctgt tttttatgca aaatctaatt taatatattg    120
atatttatat cattttacgt ttctcgttca gctttatttc attaagttgg cattataaaa    180
aagcattgct tatcaatttg ttgcaacgaa caggtcacta tcagtcaaaa taaaatcatt    240
atttgatttc aattttgtcc cactccctcc cgaattctac cgggtagggg aggcgctttt    300
cccaaggcag tctggagcat gcgctttagc agccccgctg gcacttggcg ctacacaagt    360
ggcctctggc ctcgcacaca ttccacatcc accggtagcg ccaaccggct ccgttctttg    420
gtggcccctt cgcgccactt ctactcctcc cctagtcagg aagtttcccc cccgccccgc    480
agctcgcgtc gtgcaggacg tgacaaatgg aagtagcacg tctcactagt ctcgtgcaga    540
tggacagcac cgctgagcaa tggaagcggg taggcctttg gggcagcggc caatagcagc    600
tttgctcctt cgctttctgg gctcagaggc tgggaagggg tgggtccggg ggcgggctca    660
ggggcgggct caggggcggg gcgggcgccc gaaggtcctc cggaggcccg gcattctgca    720
cgcttcaaaa gcgcacgtct gccgcgctgt tctcctcttc ctcatctccg ggcctttcga    780
ccaattcgct gtctgcgagg gccagctgtt ggggtgagta ctccctctca aaagcgggca    840
tgacttctgc gctaagattg tcagtttcca aaaacgagga ggatttgata ttcacctggc    900
ccgcggtgat gcctttgagg gtggccgcgt ccatctggtc agaaaagaca atctttttgt    960
tgtcaagctt gaggtgtggc aggcttgaga tctggccata cacttgagtg acaatgacat   1020
ccactttgcc tttctctcca caggtgtcca ctcccaggtc caactgcaga tgaccgagta   1080
caagcccacg gtgcgcctcg ccacccgcga cgacgtcccc cgggccgtac gcaccctcgc   1140
cgccgcgttc gccgactacc ccgccacgcg ccacaccgtc gacccggacc gccacatcga   1200
gcgggtcacc gagctgcaag aactcttcct cacgcgcgtc gggctcgaca tcggcaaggt   1260
gtgggtcgcg gacgacggcg ccgcggtggc ggtctggacc acgccggaga gcgtcgaagc   1320
gggggcggtg ttcgccgaga tcggcccgcg catggccgag ttgagcggtt cccggctggc   1380
cgcgcagcaa cagatggaag gcctcctggc gccgcaccgg cccaaggagc ccgcgtggtt   1440
cctggccacc gtcggcgtct cgcccgacca ccagggcaag ggtctgggca gcgccgtcgt   1500
gctccccgga gtggaggcgg ccgagcgcgc cggggtgccc gccttcctgg agacctccgc   1560
gccccgcaac ctccccttct acgagcggct cggcttcacc gtcaccgccg acgtcgaggt   1620
gcccgaagga ccgcgcacct ggtgcatgac ccgcaagccc ggtgcctgat ctagagctcg   1680
ctgatcagcc tcgactgtgc cttctagttg ccagccatct gttgtttgcc cctcccccgt   1740
gccttccttg accctggaag gtgccactcc cactgtcctt tcctaataaa atgaggaaat   1800
tgcatcgcat tgtctgagta ggtgtcattc tattctgggg ggtggggtgg ggcaggacag   1860
caagggggag gattgggaag acaatagcag gcatgctggg gatgcggtgg gctctatggc   1920
ttctgaggcg gaaagaacca gctggggctc gagatccact agttctagcc tcgaggctag   1980
agcggccgcc accgcggtgg agctccaatt cgccctatag tgagtcgtat tacgcgcgct   2040
cactggccgt cgttttacaa cgtcgtgact gggaaaaccc tggcgttacc caacttaatc   2100
gccttgcagc acatccccct ttcgccagct ggcgtaatag cgaagaggcc cgcaccgatc   2160
gcccttccca acagttgcgc agcctgaatg gcgaatggga cgcgccctgt agcggcgcat   2220
taagcgcggc gggtgtggtg gttacgcgca gcgtgaccgc tacacttgcc agcgccctag   2280
cgcccgctcc tttcgctttc ttcccttcct ttctcgccac gttcgccggc tttccccgtc   2340
```

-continued

```
aagctctaaa tcgggggctc cctttagggt tccgatttag tgctttacgg cacctcgacc   2400
ccaaaaaact tgattagggt gatggttcac gtagtgggcc atcgccctga tagacggttt   2460
ttcgcccttt gacgttggag tccacgttct ttaatagtgg actcttgttc caaactggaa   2520
caacactcaa ccctatctcg gtctattctt ttgatttata agggattttg ccgatttcgg   2580
cctattggtt aaaaaatgag ctgatttaac aaaaatttaa cgcgaatttt aacaaaatat   2640
taacgcttac aatttaggtg gcacttttcg gggaaatgtg cgcggaaccc ctatttgttt   2700
atttttctaa atacattcaa atatgtatcc gctcatgaga caataaccct gataaatgct   2760
tcaataatat tgaaaaagga agagtatgag tattcaacat ttccgtgtcg cccttattcc   2820
cttttttgcg gcattttgcc ttcctgtttt tgctcaccca gaaacgctgg tgaaagtaaa   2880
agatgctgaa gatcagttgg gtgcacgagt gggttacatc gaactggatc tcaacagcgg   2940
taagatcctt gagagttttc gccccgaaga acgttttcca atgatgagca cttttaaagt   3000
tctgctatgt ggcgcggtat tatcccgtat tgacgccggg caagagcaac tcggtcgccg   3060
catacactat tctcagaatg acttggttga gtactcacca gtcacagaaa agcatcttac   3120
ggatggcatg acagtaagag aattatgcag tgctgccata accatgagtg ataacactgc   3180
ggccaactta cttctgacaa cgatcggagg accgaaggag ctaaccgctt ttttgcacaa   3240
catgggggat catgtaactc gccttgatcg ttgggaaccg gagctgaatg aagccatacc   3300
aaacgacgag cgtgacacca cgatgcctgt agcaatggca acaacgttgc gcaaactatt   3360
aactggcgaa ctacttactc tagcttcccg gcaacaatta atagactgga tggaggcgga   3420
taaagttgca ggaccacttc tgcgctcggc ccttccggct ggctggttta ttgctgataa   3480
atctggagcc ggtgagcgtg ggtctcgcgg tatcattgca gcactggggc cagatggtaa   3540
gccctcccgt atcgtagtta tctacacgac ggggagtcag gcaactatgg atgaacgaaa   3600
tagacagatc gctgagatag gtgcctcact gattaagcat tggtaactgt cagaccaagt   3660
ttactcatat atactttaga ttgatttaaa acttcatttt taatttaaaa ggatctaggt   3720
gaagatcctt tttgataatc tcatgaccaa aatcccttaa cgtgagtttt cgttccactg   3780
agcgtcagac cccgtagaaa agatcaaagg atcttcttga gatccttttt ttctgcgcgt   3840
aatctgctgc ttgcaaacaa aaaaaccacc gctaccagcg gtggtttgtt tgccggatca   3900
agagctacca actctttttc cgaaggtaac tggcttcagc agagcgcaga taccaaatac   3960
tgtccttcta gtgtagccgt agttaggcca ccacttcaag aactctgtag caccgcctac   4020
atacctcgct ctgctaatcc tgttaccagt ggctgctgcc agtggcgata agtcgtgtct   4080
taccgggttg gactcaagac gatagttacc ggataaggcg cagcggtcgg gctgaacggg   4140
gggttcgtgc acacagccca gcttggagcg aacgacctac accgaactga gatacctaca   4200
gcgtgagcta tgagaaagcg ccacgcttcc cgaagggaga aaggcggaca ggtatccggt   4260
aagcggcagg gtcggaacag gagagcgcac gagggagctt ccagggggaa acgcctggta   4320
tctttatagt cctgtcgggt ttcgccacct ctgacttgag cgtcgatttt tgtgatgctc   4380
gtcagggggg cggagcctat ggaaaaacgc cagcaacgcg gcctttttac ggttcctggc   4440
cttttgctgg ccttttgctc acatgttctt tcctgcgtta tcccctgatt ctgtggataa   4500
ccgtattacc gcctttgagt gagctgatac cgctcgccgc agccgaacga ccgagcgcag   4560
cgagtcagtg agcgaggaag cggaagagcg cccaatacgc aaaccgcctc tccccgcgcg   4620
ttggccgatt cattaatgca gctggcacga caggtttccc gactggaaag cgggcagtga   4680
gcgcaacgca attaatgtga gttagctcac tcattaggca ccccaggctt tacactttat   4740
```

gcttccggct cgtatgttgt gtggaattgt gagcggataa caatttcaca caggaaacag 4800
ctatgaccat gattacgcca agcgcgcaat taaccctcac taaagggaac aaaagctggg 4860
taccgggccc cccctcgagg tcgacggtat cgataagctt gatatc 4906

<210> SEQ ID NO 30
<211> LENGTH: 5308
<212> TYPE: DNA
<213> ORGANISM: Artificial Sequence
<220> FEATURE:
<223> OTHER INFORMATION: pCMVssKZ-IntC3-CNLS (integrase expression plasmid)

<400> SEQUENCE: 30
gaattcctca catgttcttt cctgcgttat cccctgattc tgtggataac cgtattaccg 60
ccatgcatta gttattaata gtaatcaatt acggggtcat tagttcatag cccatatatg 120
gagttccgcg ttacataact tacggtaaat ggcccgcctg gctgaccgcc caacgacccc 180
cgcccattga cgtcaataat gacgtatgtt cccatagtaa cgccaatagg gactttccat 240
tgacgtcaat gggtggagta tttacggtaa actgcccact tggcagtaca tcaagtgtat 300
catatgccaa gtacgccccc tattgacgtc aatgacggta aatggcccgc ctggcattat 360
gcccagtaca tgaccttatg ggactttcct acttggcagt acatctacgt attagtcatc 420
gctattacca tggtgatgcg gttttggcag tacatcaatg ggcgtggata gcggtttgac 480
tcacggggat ttccaagtct ccaccccatt gacgtcaatg ggagtttgtt ttggcaccaa 540
aatcaacggg actttccaaa atgtcgtaac aactccgccc cattgacgca aatgggcggt 600
aggcgtgtac ggtgggaggt ctatataagc agagctggtt tagtgaaccg tcagatccgc 660
tagcaattcg ctgtctgcga gggccagctg ttggggtgag tactccctct caaaagcggg 720
catgacttct gcgctaagat tgtcagtttc caaaaacgag gaggatttga tattcacctg 780
gcccgcggtg atgcctttga gggtggccgc gtccatctgg tcagaaaaga caatcttttt 840
gttgtcaagc ttgaggtgtg gcaggcttga gatctggcca tacacttgag tgacaatgac 900
atccactttg cctttctctc cacaggtgtc cactcccagg tccaactgca gctcgaggtc 960
caccatggga agaaggcgaa gtcatgagcg ccgggattta cccccctaacc tttatataag 1020 aaacaatgga tattactgct acagggaccc aaggacgggt aaagagtttg gattaggcag 1080
agacaggcga ttcgcaatca ctgaagctat acaggccaac attgagttat tttcaggaca 1140
caaacacaag cctctgacag cgagaatcaa cagtgataat tccgttacgt tacattcatg 1200
gcttgatcgc tacgaaaaaa tcctggccag cagaggaatc aagcagaaga cactcataaa 1260
ttacatgagc aaaattaaag caataaggag ggtctgcct gatgctccac ttgaagacat 1320
caccacaaaa gaaattgcgg caatgctcaa tggatacata gacgagggca aggcggcgtc 1380
agccaagtta atcagatcaa cgctgagcga tgcattccga gaggcaatag ctgaaggcca 1440
tataacaaca aaccatgtcg ctgccactcg cgcggcaaag tcaaaggtaa ggagatcaag 1500
acttacggct gacgaatacc tgaaaattta tcaagcagca gaatcatcac catgttggct 1560
cagacttgca atggaactgg ctgttgttac cgggcaacga gttggtgact tgtgcaaaat 1620
gaagtggtct gatatcgtag atggatatct ttatgtcgag caaagcaaaa caggcgtaaa 1680
aattgccatc ccaacagcat tgcatattga tgctctcgga atatcaatga aggaaacact 1740
tgataaatgc aaagagattc ttggcggaga aaccataatt gcatctactc gtcgcgaacc 1800
gctctcatcc ggcacagtat caaggtattt tatgcgcgca cgaaaagcat caggtctttc 1860

-continued

```
cttcgaaggg gatccgccta cctttcacga gttgcgcagt ttgtctgcaa gactctatgg   1920
gaagcagata agcgataagt ttgctcaaca tcttctcggg cataagtcgg tcaccatggc   1980
atcacagtat cgtgatgaca gaggcaggga gtgggacaaa attgaaatca aatccggagg   2040
cggccctaag aagaagagaa aggtatgata atctagagct cgctgatcag cctcgactgt   2100
gccttctagt tgccagccat ctgttgtttg cccctccccc gtgccttcct tgaccctgga   2160
aggtgccact cccactgtcc tttcctaata aaatgaggaa attgcatcgc attgtctgag   2220
taggtgtcat tctattctgg ggggtggggt ggggcaggac agcaaggggg aggattggga   2280
agacaatagc aggcatgctg gggatgcggt gggctctatg gcttctgagg cggaaagaac   2340
cagctggggc tcgagatcca ctagttctag cctcgaggct agagcggccg ccaccgcggt   2400
ggagctccaa ttcgccctat agtgagtcgt attacgcgcg ctcactggcc gtcgttttac   2460
aacgtcgtga ctgggaaaac cctggcgtta cccaacttaa tcgccttgca gcacatcccc   2520
ctttcgccag ctggcgtaat agcgaagagg cccgcaccga tcgcccttcc caacagttgc   2580
gcagcctgaa tggcgaatgg gacgcgccct gtagcggcgc attaagcgcg gcgggtgtgg   2640
tggttacgcg cagcgtgacc gctacacttg ccagcgccct agcgcccgct cctttcgctt   2700
tcttcccttc ctttctcgcc acgttcgccg gctttccccg tcaagctcta aatcgggggc   2760
tccctttagg gttccgattt agtgctttac ggcacctcga ccccaaaaaa cttgattagg   2820
gtgatggttc acgtagtggg ccatcgccct gatagacggt ttttcgccct ttgacgttgg   2880
agtccacgtt ctttaatagt ggactcttgt tccaaactgg aacaacactc aaccctatct   2940
cggtctattc ttttgattta taagggattt tgccgatttc ggcctattgg ttaaaaaatg   3000
agctgattta acaaaaattt aacgcgaatt ttaacaaaat attaacgctt acaatttagg   3060
tggcactttt cggggaaatg tgcgcggaac ccctatttgt ttatttttct aaatacattc   3120
aaatatgtat ccgctcatga gacaataacc ctgataaatg cttcaataat attgaaaaag   3180
gaagagtatg agtattcaac atttccgtgt cgcccttatt cccttttttg cggcattttg   3240
ccttcctgtt tttgctcacc cagaaacgct ggtgaaagta aaagatgctg aagatcagtt   3300
gggtgcacga gtgggttaca tcgaactgga tctcaacagc ggtaagatcc ttgagagttt   3360
tcgccccgaa gaacgttttc caatgatgag cacttttaaa gttctgctat gtggcgcggt   3420
attatcccgt attgacgccg ggcaagagca actcggtcgc cgcatacact attctcagaa   3480
tgacttggtt gagtactcac cagtcacaga aaagcatctt acggatggca tgacagtaag   3540
agaattatgc agtgctgcca taaccatgag tgataacact gcggccaact tacttctgac   3600
aacgatcgga ggaccgaagg agctaaccgc ttttttgcac aacatggggg atcatgtaac   3660
tcgccttgat cgttgggaac cggagctgaa tgaagccata ccaaacgacg agcgtgacac   3720
cacgatgcct gtagcaatgg caacaacgtt gcgcaaacta ttaactggcg aactacttac   3780
tctagcttcc cggcaacaat taatagactg gatggaggcg gataaagttg caggaccact   3840
tctgcgctcg gcccttccgg ctggctggtt tattgctgat aaatctggag ccggtgagcg   3900
tgggtctcgc ggtatcattg cagcactggg gccagatggt aagccctccc gtatcgtagt   3960
tatctacacg acggggagtc aggcaactat ggatgaacga aatagacaga tcgctgagat   4020
aggtgcctca ctgattaagc attggtaact gtcagaccaa gtttactcat atatacttta   4080
gattgattta aaacttcatt tttaatttaa aaggatctag gtgaagatcc tttttgataa   4140
tctcatgacc aaaatccctt aacgtgagtt ttcgttccac tgagcgtcag accccgtaga   4200
```

-continued

```
aaagatcaaa ggatcttctt gagatccttt ttttctgcgc gtaatctgct gcttgcaaac   4260

aaaaaaacca ccgctaccag cggtggtttg tttgccggat caagagctac caactctttt   4320

tccgaaggta actggcttca gcagagcgca gataccaaat actgtccttc tagtgtagcc   4380

gtagttaggc caccacttca agaactctgt agcaccgcct acatacctcg ctctgctaat   4440

cctgttacca gtggctgctg ccagtggcga taagtcgtgt cttaccgggt tggactcaag   4500

acgatagtta ccggataagg cgcagcggtc gggctgaacg gggggttcgt gcacacagcc   4560

cagcttggag cgaacgacct acaccgaact gagataccta cagcgtgagc tatgagaaag   4620

cgccacgctt cccgaaggga gaaaggcgga caggtatccg gtaagcggca gggtcggaac   4680

aggagagcgc acgagggagc ttccaggggg aaacgcctgg tatctttata gtcctgtcgg   4740

gtttcgccac ctctgacttg agcgtcgatt tttgtgatgc tcgtcagggg ggcggagcct   4800

atggaaaaac gccagcaacg cggccttttt acggttcctg gccttttgct ggccttttgc   4860

tcacatgttc tttcctgcgt tatcccctga ttctgtggat aaccgtatta ccgcctttga   4920

gtgagctgat accgctcgcc gcagccgaac gaccgagcgc agcgagtcag tgagcgagga   4980

agcggaagag cgcccaatac gcaaaccgcc tctccccgcg cgttggccga ttcattaatg   5040

cagctggcac gacaggtttc ccgactggaa agcgggcagt gagcgcaacg caattaatgt   5100

gagttagctc actcattagg caccccaggc tttacacttt atgcttccgg ctcgtatgtt   5160

gtgtggaatt gtgagcggat aacaatttca cacaggaaac agctatgacc atgattacgc   5220

caagcgcgca attaaccctc actaaaggga acaaaagctg ggtaccgggc ccccctcga   5280

ggtcgacggt atcgataagc ttgatatc                                      5308
```

<210> SEQ ID NO 31
<211> LENGTH: 21
<212> TYPE: DNA
<213> ORGANISM: Artificial Sequence
<220> FEATURE:
<223> OTHER INFORMATION: attH4X attachment site

<400> SEQUENCE: 31

```
acgctttatt tcattaagtt g                                               21
```

<210> SEQ ID NO 32
<211> LENGTH: 1655
<212> TYPE: DNA
<213> ORGANISM: Artificial Sequence
<220> FEATURE:
<223> OTHER INFORMATION: Integrant E. coli colony generated using C3 harbouring the lactamase cassette

<400> SEQUENCE: 32

```
tgaatccgtt gaagcctgct tttttatact aagttggcat tataaaaaag cattgcttat     60

caatttgttg caacgaacag gtcactatca gtcaaaataa aatcattatt tgatttcccg    120

gtgatgttca ggtggcactt ttcggggaaa tgtgcgcgga acccctattt gtttattttt    180

ctaaatacat tcaaatatgt atccgctcat gagacaataa ccctgataaa tgcttcaata    240

atattgaaaa aggaagagta tgagtattca acatttccgt gtcgccctta ttcccttttt    300

tgcggcattt tgccttcctg tttttgctca cccagaaacg ctggtgaaag taaaagatgc    360

tgaagatcag ttgggtgcac gagtgggtta catcgaactg gatctcaaca gcggtaagat    420

ccttgagagt tttcgccccg aagaacgttt tccaatgatg agcactttta aagttctgct    480

atgtggcgcg gtattatccc gtattgacgc cgggcaagag caactcggtc gccgcataca    540
```

-continued

```
ctattctcag aatgacttgg ttgagtactc accagtcaca gaaaagcatc ttacggatgg    600

catgacagta agagaattat gcagtgctgc cataaccatg agtgataaca ctgcggccaa    660

cttacttctg acaacgatcg gaggaccgaa ggagctaacc gcttttttgc acaacatggg    720

ggatcatgta actcgccttg atcgttggga accggagctg aatgaagcca taccaaacga    780

cgagcgtgac accacgatgc ctgcagcaat ggcaacaacg ttgcgcaaac tattaactgg    840

cgaactactt actctagctt cccggcaaca attaatagac tggatggagg cggataaagt    900

tgcaggacca cttctgcgct cggcccttcc ggctggctgg tttattgctg ataaatctgg    960

agccggtgag cgtgggtctc gcggtatcat tgcagcactg gggccagatg gtaagccctc   1020

ccgtatcgta gttatctaca cgacggggag tcaggcaact atggatgaac gaaatagaca   1080

gatcgctgag ataggtgcct cactgattaa gcattggtaa ctgtcagacc aagtttactc   1140

atatatactt tagattgatt taaaacttca tttttaattt aaaaggatct aggtgaagat   1200

cctttttgat aatctcatga ccaaaatccc ttaacgtgag ttttcgttcc actgagcgtc   1260

agaccccgta gaaaagatca aaggatcttc ttgagatcct ttttttctgc gcgtaatctg   1320

ctgcttgcaa acaaaaaaac caccgctacc agcggtggtt tgtttgccgg atcaagagct   1380

accaactctt ttccgaaggt aactggcttc agcagagcgc agataccaaa tactgtcctt   1440

ctagtgtagg aattccacag aattccgtct gttacaggtc actaatacca tctaagtagt   1500

tgattcatag tgactgcata tattgtgttt tacagtatta tgtagtctgt tttttatgca   1560

aaatctaatt taatatattg atatttatat cattttacgt ttctcgttca gcttttttat   1620

actaacttga gcgaaacggg aaggtaaaaa gacat                              1655
```

<210> SEQ ID NO 33
<211> LENGTH: 558
<212> TYPE: DNA
<213> ORGANISM: Artificial Sequence
<220> FEATURE:
<223> OTHER INFORMATION: attL recombinant HT1080 clone 3

<400> SEQUENCE: 33

```
ctttatgacc cagtcatcgt tggtttggtc ttttcacata gtcccatgtt tcttggagat     60

tttgttcatt ccttctcatt ctttttctc taatcttgtc ctcatgcttt atttcattaa    120

gttggcatta taaaaaagca ttgcttatca atttgttgca acgaacaggt cactatcagt    180

caaaatacaa tcattatttg atttcaattt tgtcccactc cctcccgaat tctaccgggt    240

aggggaggcg cttttcccaa ggcagtctgg agcatgcgct ttagcagccc cgctgggcac    300

ttggcgctac acaagtggcc tctggcctcg cacacattcc acatccaccg gtaggcgcca    360

accggctccg ttctttggtg gccccttcgc gccaccttct actcctcccc tagtcaggaa    420

gttccccccc gccccgcagc tcgcgtcgtg caggacgtga caaatggaag tagcacgtct    480

cactagtctc gtgcagatgg acagcaccgc tgagcaatgg aagcgggtag gcctttgggg    540

cagcggccaa tagcagct                                                 558
```

<210> SEQ ID NO 34
<211> LENGTH: 558
<212> TYPE: DNA
<213> ORGANISM: Artificial Sequence
<220> FEATURE:
<223> OTHER INFORMATION: attL recombinant HT1080 clone 19

<400> SEQUENCE: 34

```
gattcggtaa ccaatcaaat gtaagcttgg tcttttcaca taatcccata tttttggag     60
```

-continued

```
gctttgttca tttcttttca ttcttttttc tctaatctgt cttcatgctt tatttcatta    120

agttggcatt ataaaaaagc attgcttatc aatttgttgc aacgaacagg tcactatcag    180

tcaaaataca atcattattt gatttcaatt ttgtcccact ccctcccgaa ttctaccggg    240

taggggaggc gcttttccca aggcagtctg gagcatgcgc tttagcagcc ccgctgggca    300

cttggcgcta cacaagtggc ctctggcctc gcacacattc cacatccacc ggtaggcgcc    360

aaccggctcc gttctttggt ggccccttcg cgccaccttc tactcctccc ctagtcagga    420

agttcccccc cgccccgcag ctcgcgtcgt gcaggacgtg acaaatggaa gtagcacgtc    480

tcactagtct cgtgcagatg gacagcaccg ctgagcaatg gaagcgggta ggcctttggg    540

gcagcggcca atagcagc                                                  558
```

MUTANTS OF THE BACTERIOPHAGE LAMBDA INTEGRASE

CROSS-REFERENCE TO RELATED APPLICATIONS

This patent application is a U.S. National Phase Application under 35 U.S.C. § 371 of International Application No. PCT/SG2015/050255, filed Aug. 11, 2015, MUTANTS OF THE BACTERIOPHAGE LAMBDA INTEGRASE, which claims priority to Great Britain Patent Application No. 1414130.3, filed Aug. 8, 2014.

INCORPORATION BY REFERENCE

This application incorporates by reference the material (i.e., Sequence Listing) in the ASCII text file named 9322P054 SequenceLstg.txt, created on Jul. 26 2017, having a file size of 40,733 bytes.

TECHNICAL FIELD

The present invention relates to mutants of bacteriophage lambda integrases and to nucleic acid molecules comprising a nucleotide sequence encoding such mutants.

BACKGROUND

Phage integrases are enzymes that mediate unidirectional site-specific recombination between two DNA recognition sequences, the phage attachment site, attP, and the bacterial attachment site, attB. Integrases may be grouped into two major families, the tyrosine recombinases and the serine recombinases, based on their mode of catalysis.

Tyrosine family integrases, such as lambda integrase, utilize a catalytic tyrosine to mediate strand cleavage, tend to recognize longer attP sequences, and require other proteins encoded by the phage or the host bacteria.

Phage integrases from the serine family are larger, use a catalytic serine for strand cleavage, recognize shorter attP sequences, and do not require host cofactors. Phage integrases mediate efficient site-specific recombination between two different sequences that are relatively short, yet long enough to be specific on a genomic scale.

These properties give phage integrases growing importance for the genetic manipulation of living eukaryotic cells, especially those with large genomes such as mammals and most plants, for which there are few tools for precise manipulation of the genome.

The use of lambda integrases has been subject to extensive research for catalyzing site-specific DNA recombination. For example, two mutant lambda integrases, Int-h (E174K) and its derivative Int-h/218 (E174K/E218K) have been described and were shown to catalyze intermolecular recombination reactions at least as efficiently as the corresponding intramolecular recombination reactions in human cells. Although the presence of arm-site sequences have been shown to increase the recombination of core-sites by Int-h/218 in vivo, given the absence of an attB site in the human genome, recombination reactions occur in non-cognate sites in an essentially random manner.

This makes it difficult to engineer cell lines in a controlled, reproducible fashion.

Therefore, there remains a need to provide mutant integrases having greater efficiency and specificity in catalyzing site specific recombination reactions.

SUMMARY

In one aspect, there is provided a lambda integrase comprising at least one amino acid mutation selected from the group consisting of I43F, E319G and D336V.

In another aspect, there is provided a lambda integrase comprising an amino acid mutation at at least one of positions 336, 319 and 43 of the lambda integrase as set forth in SEQ ID NO: 1

In another aspect, there is provided a nucleic acid molecule. The nucleic acid molecule includes a nucleotide sequence encoding a mutant as described herein.

In a further aspect, there is provided a host cell. The host cell includes a nucleic acid molecule as described herein.

In yet another aspect, there is provided a method of recombining a nucleic acid of interest into a target nucleic acid. The method includes contacting a targeting nucleic acid comprising the nucleic acid of interest with the target nucleic acid in the presence of a mutant as described herein.

In yet a further aspect, there is provided a sequence specific recombination kit. The kit includes a targeting nucleic acid into which a nucleic acid of interest can be inserted, and a mutant as described herein.

Definitions

The following words and terms used herein shall have the meaning indicated:

The term "mutant" refers to a protein arising as a result of a mutation or a recombinant DNA procedure.

The term "Int" or "integrase" refers to the lambda phage integrase protein.

As used herein, "nucleic acid" refers to any nucleic acid in any possible configuration, such as linearized single stranded, double stranded or a combination thereof. Nucleic acids may include, but are not limited to DNA molecules (e.g., cDNA or genomic DNA), RNA molecules (e.g., mRNA), analogues of the DNA or RNA generated using nucleotide analogues or using nucleic acid chemistry, cDNA synthetic DNA, a copolymer of DNA and RNA, oligonucleotides, and PNA (protein nucleic acids). DNA or RNA may be of genomic or synthetic origin and may be single or double stranded. A respective nucleic acid may furthermore contain non-natural nucleotide analogues and/or be linked to an affinity tag or a label.

As used herein, nucleotides include nucleoside mono-, di-, and triphosphates. Nucleotides also include modified-nucleotides, such as, but not limited to, phophorothioate nucleotides and deazapurine nucleotides and other nucleotide analogs.

An "attB/attP reaction" or a "B/P reaction" is a recombination reaction between an attB recognition site and an attP recognition site mediated by an Int.

An "attH/attPH reaction" or an "H/PH reaction" is a recombination reaction between an attH recognition site and an attPH recognition site mediated by an Int.

An "att site" is an attachment site on a DNA molecule for an integrase or integrase complex. As used herein, "att site" is generally used interchangeably with "recognition site," described in greater detail below. Generally, "att site" is used to refer to a particular type of recognition site, such as, for example, an attB, an attP, an attL, or an attR site.

"Chromosomally-integrated" or "integrated" refers to the integration of a foreign gene or nucleotide sequence into a host genome by covalent bonds that are formed with the host DNA.

"Deletion reaction" and "excision reaction" are used interchangeably and refer to a recombination reaction between two recognition sites that are on the same DNA molecule and are in direct orientation with respect to one another. This reaction results in the removal of a nucleotide sequence that is positioned between the two recognition sites.

"Direct orientation" refers to an orientation of two or more recognition sites such that 15 base pair core regions of the recognition sites are oriented in the same 5' to 3' direction. "Direct repeat," as used herein, refers to two or more recognition sites that are in direct orientation with respect to each other.

"Donor," "donor molecule," "donor sequence," and "donor DNA" are used interchangeably to refer to a nucleotide sequence that has been selected to undergo recombination with the target DNA sequence using site-directed recombination. The donor nucleotide sequence can be any nucleotide sequence, such as, for example, a gene, an expression cassette, a promoter, a molecular marker, a selectable marker, a visible marker, a portion of any of these, or the like. The donor DNA sequence comprises at least one recombinase recognition site.

"Endogenous" as used herein means "of the same origin," i.e., derived from a host cell.

"Expression cassette" as used herein includes a nucleotide sequence that is capable of directing or driving the expression of another nucleotide sequence in an appropriate host cell. An expression cassette typically comprises a promoter operably linked to a nucleotide sequence, such as a nucleotide sequence of interest, for example, which is operably linked to a termination signal. The expression cassette also typically comprises sequences needed for proper translation of the nucleotide sequence. The nucleotide sequence of interest usually codes for a protein of interest but can also code for a functional RNA of interest, for example antisense RNA or a non-translated RNA that, in the sense or antisense direction, inhibits expression of a particular gene, e.g., antisense RNA. The expression cassette comprising the nucleotide sequence can be chimeric, meaning that at least one of its components is heterologous with respect to at least one of its other components. The expression cassette can include endogenous DNA that has been obtained in a recombinant form and is useful for heterologous expression. Typically, however, the expression cassette is heterologous with respect to the host; that is, the particular DNA sequence of the expression cassette does not occur naturally in the host cell and must be introduced into the host cell or an ancestor of the host cell through a transformation event. The expression of the nucleotide sequence in the expression cassette can be under the control of any suitable promoter, such as for example, either a constitutive promoter or an inducible promoter that initiates transcription only when the host cell is exposed to some particular external stimulus. In the case of a multicellular organism, the promoter can also be specific to a particular tissue or organ or stage of development.

A "foreign" gene or DNA refers to a gene or a nucleotide sequence that is not normally found in the host organism but can be introduced by gene transfer. Foreign genes and DNA that are not integrated into the genome of the host cell are referred to as "extrachromosomal."

The term "gene" is used broadly to include any segment of a nucleotide sequence associated with a biological function. Thus, a gene can include a coding sequence either with or without the regulatory sequences required for its expression. Further, a gene can include both exon and intron sequences or can include only exon sequences. A gene can also include non-expressed DNA segments that, for example, form recognition sequences for other proteins. A "portion of a gene" or "an incomplete gene" as used herein means a part of a gene that is non-functional because it does not contain all of the sequence needed for functionality. The portion can be the 5' portion of a gene (i.e., the sequence at the 3' end of the gene is not present), or the portion can be the 3' portion of a gene (i.e., the sequence at the 5' end of the gene is not present). The 5' and 3' portions can be nonfunctional on their own, but when the 5' and 3' portions are operably linked, the gene is "functional" or "complete."

"Gene of interest," "sequence of interest," "nucleic acid of interest," and "DNA of interest" are used interchangeably and include any nucleotide sequence which, when transferred to a cell, confers upon the cell a desired characteristic, such as virus resistance, insect resistance, antibiotic stress resistance, disease resistance, resistance to other pests, herbicide tolerance, improved nutritional value, improved performance in an industrial process, or altered reproductive capability, for example. The sequence of interest can also be one that is transferred to cell lines or mammals or plants for the production of commercially valuable enzymes or metabolites. In this context, the "target nucleic acid" as used herein refers to a nucleotide sequence containing at least one recognition site. The target nucleotide sequence can be a gene, an expression cassette, a promoter, a molecular marker, a portion of any of the above, or the like. The target nucleic acid can be stably transformed into a host cell to create a transformed cell line comprising the target sequence integrated into a chromosomal location in the genome. Accordingly, in some embodiments, the target nucleic acid can include genomic DNA. The genomic DNA can be comprised in a cell. In other embodiments, the target nucleic acid can include a sequence selected from the group consisting of an attH sequence (SEQ ID NO: 7) and an attH4X sequence (SEQ ID NO: 31).

"Genome" refers to the complete genetic material of an organism.

"Heterologous" as used herein means "of different natural origin," i.e., representing a non-natural state. For example, if a host cell is transformed with a gene derived from another organism, particularly from another species, that gene is heterologous with respect to both the host cell and descendants of the host cell that carry the gene. Similarly, "heterologous" refers to a nucleotide sequence which is derived from a natural or original cell type and is inserted into that same natural or original cell type, but which is present in a non-natural state, such as, for example, in a different copy number, under the control of different regulatory elements, or the like.

To "identify" a recombination product means that the recombination product is detected and distinguished from both the target and donor sequences. There are many means for identifying a recombination product. For example, a selectable marker gene can be used, whereby site-specific integration results in the selectable marker becoming operatively linked with a promoter only in a recombinant product. Alternatively, a visible marker gene can be used, whereby a gain or loss of marker gene expression identifies a recombination product. Alternatively, a negative selectable marker gene can be used, whereby a loss or lack of expression of the marker gene identifies a recombination product. Additionally, molecular markers that are characteristic of the target sequence and/or donor sequence can be used, such that the molecular marker pattern is unique for the recombination product.

"Integrase" as used herein refers to a bacteriophage lambda-derived integrase, including wild-type integrase and any of a variety of mutant or modified integrases. "Integrase complex" as used herein refers to a complex comprising integrase and integration host factor (IHF). "Integrase complex" as used herein may also refer to a complex comprising integrase, integration host factor, and a bacteriophage lambda-derived excisionase (Xis). Further, as used herein, "Int" refers to both "integrase" and "integrase complex."

An "integrase-mediated recombination product" is a recombination product formed between target and donor sequences in the presence of an integrase or integrase complex. The integrase-mediated recombination results in strand exchange between at least one recombinase recognition site on the target and at least one recombinase recognition site on the donor, whereby a recombination product is formed. Consistent with the usage defined above, "Int-mediated recombination" or "Int-mediated recombination product" means a recombination or recombination product that is mediated by either an integrase or an integrase complex.

"Intramolecular recombination" refers to recombination between recognition sites on a single nucleic acid molecule. Recombination between recognition sites on different molecules is termed "intermolecular recombination."

"Intrachromosomal recombination" refers to recombination between recognition sites on a single chromosome. Recombination between recognition sites on different chromosomes is termed "interchromosomal recombination."

An "inversion reaction" refers to an intramolecular recombination reaction between two att sites that are in inverted orientation with respect to each other. For example, an inversion reaction can be effected by an intramolecular reaction between either an attB site and an attP site in inverted orientation or an attL site and an attR site in inverted orientation.

"Inverted orientation" refers to an orientation of two recognition sites such that 15 base pair core regions of the recognition sites are oriented in the opposite 5' to 3' direction.

"Operably linked" or "operatively linked" refers to the relationship between two or more nucleotide sequences that interact physically or functionally. For example, a promoter or regulatory nucleotide sequence is said to be operably linked to a nucleotide sequence that codes for an RNA or a protein if the two sequences are situated such that the regulatory nucleotide sequence will affect the expression level of the coding or structural nucleotide sequence. A 5' portion of a gene is operatively or operably linked with a 3' portion of a gene if the two portions are situated to form a functional gene.

"Recognition site" or "recombination site" refers to a nucleotide sequence that can be recognized by a recombinase protein. The recognition site is the nucleotide sequence at which binding, cleavage, and strand exchange is performed by the recombinase and any associated accessory proteins. Integrase or integrase complex recognizes recognition sites comprising an attB, attL, attR, attP, and/or suitable mutations of such sites. The attB site can be approximately 25-30 bps and includes two 7 bp core sequences and a 7 bp overlap (or spacer) region, whereas the attP site can be approximately 240 bps and comprises binding sites for an integrase and one or more accessory proteins. The attB and attP sites can be recombined together by Int or, alternatively, the attL and attR sites can be recombined together by Int.

"Recombinase" refers to an enzyme that is capable of performing site-specific recombination of DNA. Recombinase enzymes possess endonuclease and ligase activities. A recombinase can function either as a single protein or as a part of a complex of proteins. As used herein integrase and integrase complex are recombinases.

Generally, if a recombinase-mediated recombination occurs between two recombinase recognition sites that are on the same molecule, the recombination reaction results in either the deletion or inversion of a sequence flanked by the two recognition sites. If a recombinase-mediated recombination occurs between two recombinase recognition sites that are on different molecules (e.g., between a recombinase recognition site on a target sequence and a recombinase recognition site on a donor sequence), the recombination reaction results in the insertion of a sequence from one of the molecules into the other molecule (e.g., the insertion of a donor sequence into a target molecule). When particular recognition sites that are capable of recombining are present on both the target and the donor (e.g., an attB site on the target and an attP site on the donor or an attL site on the target and an attR site on the donor), the recombination product represents an exchange of nucleotide sequence between the two sites, resulting in two new sites. Each of these new sites contains a part of the original recognition sites from both the donor and target molecules. For example, when recombination occurs between an attB site on the target and an attP site on the donor, attL and attR sites are created in the recombination products. Additionally, the newly formed attL and attR sites are flanked on one side by sequence obtained from the donor molecule and on the other side by sequence obtained from the target molecule.

"Regulatory element" includes a nucleotide sequence that is involved in conferring upon a host cell the expression of another nucleotide sequence, such as, for example, a sequence of interest. A regulatory element can comprise a promoter that is operably linked to the nucleotide sequence of interest and to a termination signal. Regulatory elements also typically encompass sequences useful for proper translation of the nucleotide sequence of interest.

"Selectable marker" or "selectable marker gene" refers to a nucleotide sequence whose expression in a cell gives the cell a selective advantage under particular conditions. The selective advantage possessed by the cell transformed with the selectable marker gene can be an improved ability to grow in the presence of a negative selective agent, such as an antibiotic or an herbicide, for example, as compared to the ability of non-transformed cells. Alternatively, the selective advantage possessed by the transformed cells can be an enhanced capacity, relative to non-transformed cells, to utilize a particular compound as a nutrient, growth factor, or energy source.

Alternatively, the selective advantage possessed by the transformed cell can be the loss of a previously possessed trait or characteristic, effecting what is termed "negative selection." In this last case, the host cell is exposed to or contacted by a compound that is toxic only to cells that have not lost the ability to express a specific trait or characteristic (such as a negative selectable marker gene, for example) that was present in the parent cell, which is typically a transgenic parent cell.

"Site-directed recombination" as used herein refers to recombination between two nucleotide sequences that each comprises at least one recognition site.

"Site-specific" means at a particular nucleotide sequence, which can be in a specific location in the genome of a host cell. The nucleotide sequence can be endogenous to the host cell, either in its natural location in the host genome or at some other location in the genome, or it can be a heterologous nucleotide sequence, which has been previously inserted into the genome of the host cell by any of a variety of known methods.

"Stably transformed" refers to a host cell that contains a nucleotide sequence of interest that has been stably integrated into the genome of the host cell.

"Target," "target molecule," "target sequence," and "target DNA" are used interchangeably to refer to a nucleotide sequence containing at least one recombinase recognition site. The target nucleotide sequence can be a gene, an expression cassette, a promoter, a molecular marker, a portion of any of these, or the like. The target sequence can be stably transformed into a cell to create a "target line" comprising the target sequence integrated into a chromosomal location in a genome.

A "targeted integration event" or "target event" refers to a recombination product formed between target and donor sequences in the presence of an integrase or integrase complex. In particular, it refers to the integration of a donor sequence into a target sequence as a consequence of an Int-mediated recombination when the target sequence is stably transformed into a cell.

A "visible marker gene" refers to a gene or nucleotide sequence whose expression in a transformed cell may not confer an advantage to that cell but can be detected or made visible. Examples of visible markers include, but are not limited to, β-glucuronidase (GUS), luciferase (LUC), and fluorescent proteins (such as green fluorescent protein (GFP) or cyan fluorescent protein (CFP), for example).

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, non-recited elements.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DISCLOSURE OF OPTIONAL EMBODIMENTS

Exemplary, non-limiting embodiments of a lambda integrase comprising at least one amino acid mutation at positions 43, 319 and 336, will now be disclosed.

In this context, mutations present in the lambda integrase described herein may comprise any mutations such as substitutions, deletions and also insertions of the natural amino acid sequence of the lambda integrase as long as the resulting polypeptide folds into a three-dimensionally stable structure and shows the desired (enhanced) recombination activity. The lambda integrase described herein may comprise conservative and/or non-conservative mutations. Examples of possible mutations are conservatively modified variations where the alteration is the substitution of an amino acid with a chemically similar amino acid. In addition to the above, the lambda integrase may comprise mutations, such as conservative mutations, outside of the regions as mentioned above. Such conservative substitutions are known to those of skill in the art and may include substitutions between: 1) alanine, serine, threonine; 2) aspartic acid and glutamic acid; 3) asparagine and glutamine; 4) arginine and lysine; 5) isoleucine, leucine, methionine, valine; and 6) phenylalanine, tyrosine, tyroptophan.

The "amino acid residue" as used herein refers to any amino acid and can either be in the D or L form or to an amino acid mimetic that can be incorporated into a polypeptide by an amide bond.

Accordingly, the positively charged amino acid residue can for example either be a naturally occurring amino acid residue that is positively charged under physiological conditions such as arginine or lysine or a non-natural mimetic such as a lysine residue the alpha-amino group of which is alkylated in order to yield a (quarternary) ammonium-salt having a permanent positive charge.

In one embodiment a lambda integrase comprising at least one amino acid substitution at positions 43, 319 and 336 of the lambda integrase as set forth in SEQ ID NO: 1.

In another embodiment, the lambda integrase as described herein comprises an amino acid substitution at positions 43, 319 and 336 of the lambda integrase as set forth in SEQ ID NO: 1.

In another embodiment, the amino acid residue isoleucine at sequence position 43 is replaced by an aromatic amino acid. The aromatic amino acid may be selected from the group consisting of phenylalanine, tyrosine and tryptophan. In one embodiment the aromatic amino acid is phenylalanine.

In another embodiment, the amino acid residue glutamate at sequence position 319 is replaced by glycine.

In another embodiment, the amino acid residue aspartate at sequence position 336 may be replaced by a hydrophobic amino acid. The hydrophobic amino acid may be an aliphatic amino acid. The aliphatic amino acid may be selected from the group consisting of isoleucine, leucine and valine. In one embodiment the aliphatic amino acid is valine.

In a further embodiment, the lambda integrase as described herein may comprise the amino acid substitutions I43F, E319G and D336V.

In an alternative embodiment, the lambda integrase as described herein may comprise an amino acid substitution at position 336 of the lambda integrase as set forth in SEQ ID NO: 1. The amino acid residue aspartate at sequence position 336 may be replaced by a hydrophobic amino acid. The hydrophobic amino acid may be an aliphatic amino acid. The aliphatic amino acid may be selected from the group consisting of isoleucine, leucine and valine. In one embodiment, the aliphatic amino acid is valine.

The mutations in the lambda integrase as described herein are generally important in directing recombinase specificity and efficiency.

The lambda integrase as described herein can be generated through various selection systems known to persons skilled in the art. For example, bacterial selection systems relying on identification of functional mutants through reporter gene activation or substrate-linked protein evolution (SLiPE) have been previously described. These selection systems are one of many different approaches for engineering altered site-specificities in recombinases. For example, a genetic selection system in yeast has also been described that yielded HIV-1 integrase variants displaying altered DNA binding affinities. As another example, in vitro compartmentalization (IVC) can be used as a selection system for generating and identifying variants such as the mutants of the invention as described herein.

The bacteriophage lambda integrase is the prototypical member of the large tyrosine-recombinase family. Generally, the bacteriophage lambda integrase comprises 3 distinct domains that collaborate within a higher-order tetrameric structure to form a dynamic recombinogenic complex. These 3 domains are the N-terminal DNA binding domain (amino acid residues 1-64); the core DNA-binding domain (amino acid residues 65-175); and the C-terminal catalytic domain (amino acid residues 176-356). The bacteriophage lambda integrase is central to the bacteriophage lifecycle, facilitating the controlled integration and excision of its genome into and out of the host bacterial chromosome, respectively. In its natural function, the bacteriophage lambda integrase is able to catalyze site-specific recombination between a pair of target sequences, termed att sites, in the absence of high-energy cofactors. The target sequences (attP in the bacteriophage genome, attB in the bacterial genome) comprise a pair of 7 bp inverted core-binding sites separated by a 7 bp “overlap” region. The “overlap region” or “overlap sequence” as used herein defines the sequence of the recombination sequences where the DNA strand exchange, including strand cleavage and re-ligation, takes place and relates to the consensus DNA sequence 5'-TTTATAC-3' in wild-type att sites or said sequence having functional nucleotide substitutions. The bacteriophage lambda integrase DNA core-binding domain primarily recognizes the 7 bp attP x attB core DNA sequence motifs. In the much longer attP site, the core sequence is flanked by binding sites for accessory DNA-bending factors such as integration host factor (IHF), factor for inversion stimulation (FIS) and excisionase (Xis). In addition to these accessory sites, several ‘arm’ binding sites for the N-terminal domain of the bacteriophage lambda integrase also flank the attP core site. Binding of the N-domain of the bacteriophage lambda integrase to ‘arm’ binding sites allosterically modulates the coupled core binding and catalytic domain to increase the affinity to core sites, which ultimately enables DNA strand cleavage and productive recombination of attB x attP. Therefore, these ‘arm’ regions are essential for activating efficient DNA cleavage by the C-terminal catalytic domain of bacteriophage lambda integrase, and thus contribute to the regulation of recombination directionality.

Generally, when a recombinase-mediated recombination occurs between two recognition sites, the recombination reaction can either occur on two different molecules or within the same molecule (e.g., between a recognition site on a target sequence and a recognition site on a donor sequence). In this context, the lambda integrase as described herein can catalyze either intermolecular or intramolecular recombination reactions or both intermolecular and intramolecular recombination reactions.

As used herein, “site-specific recombination” or “sequence-specific recombination” refers to recombination between two nucleotide sequences that each comprises at least one recognition site or at least one non-cognate site. “Site-specific” means at a particular nucleotide sequence, which can be in a specific location in the genome of a host cell for example. The nucleotide sequence can be endogenous to the host cell, either in its natural location in the host genome or at some other location in the genome, or it can be a heterologous nucleotide sequence, which has been previously inserted into the genome of the hose cell by any of a variety of known methods.

As described herein, “recognition sites” or “cognate sites” refer to a nucleotide sequence that can be recognized by a recombinase protein. The “recognition site” is the nucleotide sequence upon which binding, cleavage and strand exchange is performed by the recombinase protein and any associated accessory proteins. The lambda integrase recognizes cognate sites comprising attB, attP, attL, attR, and/or suitable mutations of such sites. The attB site and attP sites can be recombined together by the lambda integrase, or alternatively, the attL and attR sites can be recombined by the lambda integrase. In this context, the lambda integrase (Int mutants) described herein can facilitate recombination between, for example, the attB and attP sites. Advantageously, the lambda integrase described herein is able to recombine into non-cognate sites (such as the attH site) with greater efficiency, as compared to the parental Int-h/218integrase.

In another embodiment there is provided a nucleic acid molecule comprising a nucleotide sequence encoding the lambda integrase as described herein.

It will be appreciated that the degeneracy of the genetic code permits substitutions of certain codons by other codons which specify the same amino acid and hence give rise to the same protein, the invention is not limited to a specific nucleic acid molecule but includes all nucleic acid molecules comprising a nucleotide sequence coding for the lambda integrase described herein. In one embodiment, the nucleic acid molecule is operably linked to a regulatory sequence to permit expression of the nucleic acid molecule.

It will be appreciated that the precise nature of the regulatory regions needed for gene sequence expression may vary from organism to organism, but shall, in general include a promoter region which, in prokaryotes, contains only the promoter or both the promoter which directs the initiation of RNA transcription as well as the DNA sequences which, when transcribed into RNA will signal the initiation of synthesis. Such regions will normally include non-coding regions which are located 5' and 3' to the nucleotide sequence to be expressed and which are involved with initiation of transcription and translation such as the TATA box, capping sequence and CAAT sequences. These regions can for example, also contain enhancer sequences or translated signal and leader sequences for targeting the produced polypeptide to a specific compartment of a host cell, which is used for producing a recombinant lambda integrase of the present invention. In one embodiment regulatory sequence comprises a promoter sequence.

In some embodiments, a nucleic acid of the invention comprises a transcriptional initiating region functional in a cell and a transcriptional terminating region functional in a cell. Suitable promoter sequences that can be used are for example, the lac promoter, the tet-promoter or the T7 promoter in the case of bacterial expression. An example of a promoter suitable for expression in eukaryotic systems is the SV 40 promoter.

In further embodiments, the nucleic acid molecule is comprised in a vector, particularly in an expression vector. Such an expression vector can comprise, besides the above-mentioned regulatory sequences and a nucleic acid sequence which codes for a lambda integrase, a sequence coding for restriction cleavage site which adjoins the nucleic acid sequence coding for the lambda integrase in 5' and/or 3' direction. This vector also permits the introduction of another nucleic acid sequence coding for a protein to be expressed. The expression vector may also contain replication sites and control sequences derived from a species compatible with the host that is to be used for expression. The expression vector may be based on plasmids well known to person skilled in the art such as pBR322, puC16, pBluescript® and the like.

In one embodiment there is also provided a host cell containing a nucleic acid molecule. The vector containing the nucleic acid molecule can be transformed into host cells capable of expressing the genes. The transformation can be carried out in accordance with standard techniques. In this context, the transformed host cells can be cultured under conditions suitable for expression of the nucleotide sequence encoding the lambda integrase. Host cells can be established, adapted and completely cultivated under serum free conditions, and optionally in media which are free of any protein/peptide of animal origin. Commercially available media such as RPMI-1640 (Sigma), Dulbecco's Modified Eagle's Medium (DMEM; Sigma), Minimal Essential Medium (MEM; Sigma), CHO-S-SFMII (Invitrogen), serum free-CHO Medium (Sigma), and protein-free CHO Medium (Sigma) are exemplary appropriate nutrient solutions. Any of the media may be supplemented as necessary with a variety of compounds, examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that are known to those skilled in the art.

In yet another embodiment, there is provided a method of recombining a nucleic acid of interest into a target nucleic acid. The method comprises contacting a targeting nucleic acid comprising the nucleic acid of interest with the target nucleic acid in the presence of a lambda integrase as described herein.

In some embodiments, the method of recombining the nucleic acid of interest into the target nucleic acid is a sequence specific recombination. The sequence specific recombination can be performed in the presence of one or more cofactors. The cofactors can be selected from the group consisting of integration host factor (IHF), factor for inversion stimulation (FIS) and excisionase (Xis).

The "targeting nucleic acid" as used herein refers to a nucleotide sequence that contains at least one recognition site. The targeting nucleic acid can contact a target nucleic acid in the presence of a mutant of the invention, in order to recombine a nucleic acid of interest into the target nucleic acid. The targeting nucleotide sequence can be a gene, an expression cassette, a promoter, a molecular marker, a portion of any of the above, or the like. In some embodiments, the targeting nucleic acid can be a vector. In other embodiments, the targeting nucleic acid comprises a sequence selected from the group consisting of an attPH sequence (SEQ ID NO: 8) and an attP4X sequence (SEQ ID NO: 9). The term "nucleic acid of interest" as used herein refers to a polynucleotide sequence of any length that encodes a product of interest. The selected sequence can be a full length or a truncated gene, a fusion or tagged gene, and can be a cDNA, a genomic DNA, or a DNA fragment. It can also be the native sequence, i.e., naturally occurring form(s), or can be mutated or otherwise modified as desired. These modifications can include codon optimizations to optimize codon usage in the selected cell or host cell, humanization or tagging. The selected sequence can encode a secreted, cytoplasmic, nuclear, membrane bound or cell surface polypeptide. The "product of interest" can include, but are not limited to proteins, polypeptides, fragments thereof, peptides, antisense RNA, all of which can be produced in the selected host cell.

In one embodiment, the genomic DNA is comprised in a cell. The method described herein may be performed in all eukaryotic cells. Cells and cell lines may be present, for example in a cell culture and include but are not limited to eukaryotic cells, such as yeast, plant, insect or mammalian cells. For example, the cells may be oocytes, embryonic stem cells, hematopoietic stem cells or any type of differentiated cells. In certain embodiments, the method of the invention can be performed in a mammalian cell. The mammalian cell lines can include, but are not limited to a human, simian, murine, mice, rat, monkey, rabbit, rodent, hamster, goat, bovine, sheep or pig cell lines. Exemplary cell lines can include, but are not limited to Chinese hamster ovary (CHO) cells, murine myeloma cells such as NSO and Sp2/0 cells, COS cells, Hela cells and human embryonic kidney (HEK-293) cells.

The target nucleic acid may comprise DNA. The DNA may be genomic DNA.

In one embodiment, the target nucleic acid comprises a sequence selected from the group consisting of an attH sequence (SEQ ID NO: 7) and an attH4X sequence (SEQ ID NO: 31). The targeting nucleic acid may be a vector. In one embodiment, the targeting nucleic acid comprises a sequence selected from the group consisting of an attH sequence (SEQ ID NO: 7) and an attH4X sequence (SEQ ID NO: 31).

In another embodiment sequence specific recombination may be performed in the presence of one or more cofactors. The cofactors may be selected from the group consisting of XIS, FIS and IHF.

In another embodiment, there is provided a sequence specific recombination kit comprising a targeting nucleic acid into which a nucleic acid of interest can be inserted, and lambda integrase or a nucleic acid as described herein.

The kit as described herein may comprise at least one reagent for inserting a nucleic of interest into the targeting nucleic acid. The reagent may be a restriction enzyme or ligase. In another embodiment, the targeting nucleic acid may comprise a sequence selected from the group consisting of an attH sequence (SEQ ID NO: 7) and an attH4X sequence (SEQ ID NO: 31).

In one embodiment, the kit as described herein may further comprise buffer(s) and/or instructions for recombining the nucleic acid of interest with a given target nucleic acid.

In one embodiment, the kit as described herein may further comprise at least one reagent for determining successful sequence specific recombination event. In one embodiment, the reagent component is a primer pair. The primer pair may be supplied in combination with the kit or supplied separately from the kit.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 shows the sequence alignment of the core bacterial attB, and human attH and attH4X sequences. The 7 base pairs (bp) highlighted in grey represent the overlap sequence, which must be identical in both recombination partners, i.e. attB & attP, attH & attPH, attH4X and attP4X. The attH site differs from the bacterial attB site at one position in the 7 bp overlap sequence and three positions in the right arm core binding sequence. The non-cognate attH4X site occurs approximately 940 times in the human genome as part of human Line1 (long interspersed nuclear elements/remnants of retrotransposons/non-coding). The first three nucleotides of the attH4X sequence are degenerate.

FIG. 3A shows in vivo recombination of exogenous DNA (lactamase gene cassette) into the attB site of *E. coli* chromosomal DNA mediated by integrase variant C3 as determined by PCR amplification from colonies growing on 100 ug/mL (1×) and 70 ug/mL (0.7×) ampicillin plates after being transformed with appropriate minicircles described in FIG. 2. Chromosomal integration was verified using PCR primers flanking the endogenous attB site, ecoliattBF (SEQ ID NO: 16) and ecoliattBR (SEQ ID NO: 17). In absence of integration, the expected PCR product is ~200 bp (as seen for colonies 1,5,6). Integration of the lactamase gene cassette results in a PCR product of ~1650 bp (colonies 2-4, 7-10).

FIG. 3B compares integration into attB of *E. coli* mediated by parental Int-h/218 or C3 integrase. When parental Int-h/218 was used, only 2 colonies were observed (both of which, i.e. 100%, had correctly inserted lactamase cassette). In the case of C3, 27 colonies were observed. 10 of these were tested and 9 (90%) showed correctly inserted lactamase cassette. Therefore, of the colonies, we can predict that ~90% (~24 colonies) contained the correctly inserted lactamase cassette. This corresponds to an improvement of ~12 fold (24 divided by 2).

FIG. 3C shows the nucleotide sequence of an integrant *E. coli* colony generated using C3 harbouring the lactamase cassette. Bacterial chromosomal DNA flanking the cassette is in lower case. The attL and attR sites generated through recombination of attB and attP are underlined and in bold. The lactamase open reading frame is in bold.

FIG. 5A shows the intra-molecular recombination efficiency of the mutant integrases C2 without or with a C-terminal nuclear localization sequence (C2-N) of an episomal plasmid substrate in the HT1080 cell line with attB and attP sites. Y-axis denotes percentage eGFP positive cells (indicative of recombination between attB/attP sites) and activities are presented relative to the transfection efficiency as determined by EGFP vector transfection (100%). The mutant C2 recombined attB x attP more efficiently than Int-h/218.

FIG. 5B shows the intra-molecular recombination efficiency of the mutant integrases C2 without or with a C-terminal nuclear localization sequence (C2-N) of an episomal plasmid substrate in the HT1080 cell line with attH and attPH sites. Y-axis denotes percentage eGFP positive cells (indicative of recombination between attH/PH sites) and activities are presented relative to the transfection efficiency as determined by EGFP vector transfection (100%). The mutant C2 recombined attH and attPH more efficiently than Int-h/218.

FIG. 5C shows the intra-molecular recombination efficiency of the mutant integrases of an episomal plasmid substrate in the HT1080 cell line with attB and attP sites. Y-axis denotes percentage eGFP positive cells (indicative of recombination between attB/attP sites) and activities are presented relative to the transfection efficiency as determined by EGFP vector transfection (100%). The mutant C3 recombined attB x attP more efficiently than Int-h/218 or a codon-optimized Int-h/218 (opt Int).

FIG. 5D shows the intra-molecular recombination efficiency of the mutant integrase C3 of an episomal plasmid substrate in the HT1080 cell line with attH and attPH sites. Y-axis denotes percentage eGFP positive cells (indicative of recombination between attH/PH sites) and activities are presented relative to the transfection efficiency as determined by EGFP vector transfection (100%). The mutant C3 recombined attH and attPH more efficiently than Int-h/218 or a codon-optimized Int-h/218 (opt Int).

FIG. 6B shows the nucleotide sequence of attL site generated through recombination between the attH4x and attP4x in the HT1080 clones 3 and 19. Human genomic DNA sequence flanking the attL sequence is in lower case. HOP' sequence is in italics, bold and underlined. The attL sequence is underlined and in bold. The PGK promoter sequence (part of the pPGKssPuro-attP4x targeting vector and driving the expression of Puromycin resistance gene) is in upper case. Genomic locus of the targeted attH4x sequence in each clone is specified.

EXAMPLES

Figure 2:
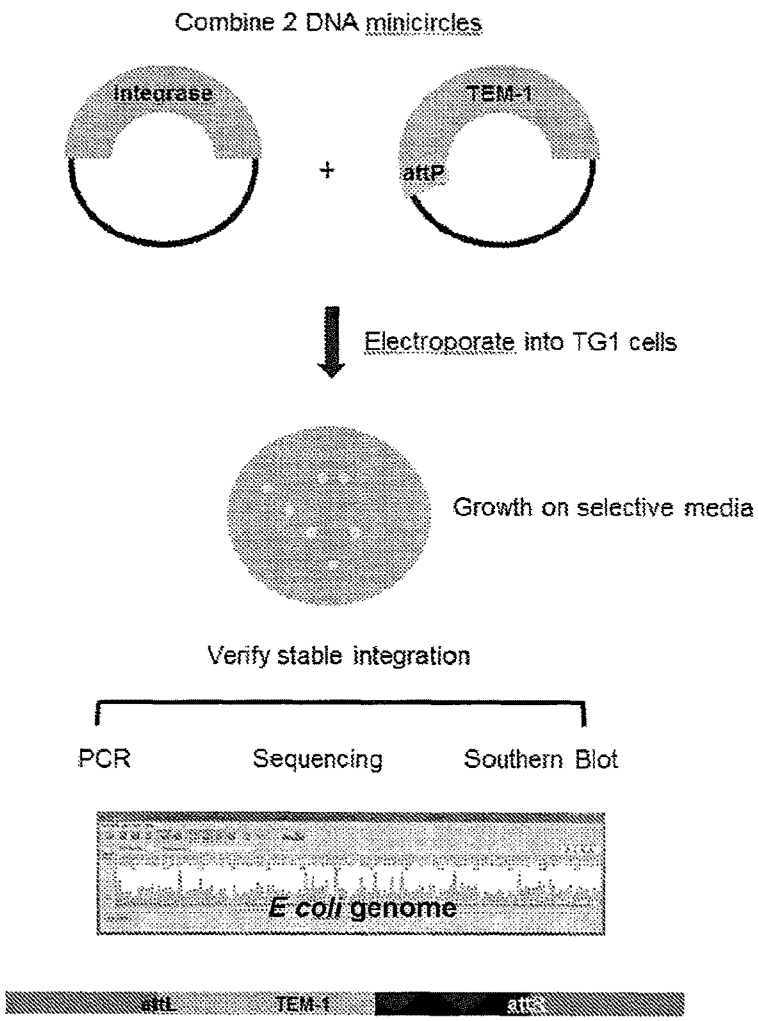
FIG. 2 shows the methodology for Rapid *E. coli* Chromosomal Integration using DNA minicircles and lambda integrase technology. The first step is to create a minicircle comprising lambda integrase under control of a suitable promoter (e.g. T7), and a minicircle comprising gene to be stably integrated, a selectable marker for antibiotic resistance (e.g. lactamase gene cassette) and the attP sequence. The second step is to transform both minicircles by electroporation or heat shock into *E. coli*, and then to plate and culture on selectable media (eg ampicillin plates). The third step is to confirm integration into attB site by PCR, sequencing and Southern blot.

Non-limiting examples of the invention, including the best mode, and a comparative example will be further described in greater detail by reference to specific Examples, which should not be construed as in any way limiting the scope of the invention.

Materials

SEQ ID NO: 1
Int-h/218
MGRRRSHERRDLPPNLYIRNNGYYCYRDPRTGKEFGLGRDRRIAITEAIQANIELFSG
HKHKPLTARINSDNSVTLHSWLDRYEKILASRGIKQKTLINYMSKIKAIRRGLPDAPL
EDITTKEIAAMLNGYIDEGKAASAKLIRSTLSDAFREAIAEGHITTNHVAATRAAKSK
VRRSRLTADEYLKIYQAAESSPCWLRLAMELAVVTGQRVGDLCKMKWSDIVDGYLYVE
QSKTGVKIAIPTALHIDALGISMKETLDKCKEILGGETIIASTRREPLSSGTVSRYFM
RARKASGLSFEGDPPTFHELRSLSARLYEKQISDKFAQHLLGHKSDTMASQYRDDRGR
EWDKIEIK

SEQ ID NO: 2
C2 integrase mutant:
MGRRRSHERRDLPPNLYIRNNGYYCYRDPRTGKEFGLGRDRRIAITEAIQANIELFSG
HKHKPLTARINSDNSVTLHSWLDRYEKILASRGIKQKTLINYMSKIKAIRRGLPDAPL
EDITTKEIAAMLNGYIDEGKAASAKLIRSTLSDAFREAIAEGHITTNHVAATRAAKSK
VRRSRLTADEYLKIYQAAESSPCWLRLAMELAVVTGQRVGDLCKMKWSDIVDGYLYVE
QSKTGVKIAIPTALHIDALGISMKETLDKCKEILGGETIIASTRREPLSSGTVSRYFM
RARKASGLSFEGDPPTFHELRSLSARLYEKQISDKFAQHLLGHKSVTMASQYRDDRGR
EWDKIEIK SEQ ID NO: 3
C3 integrase mutant:
MGRRRSHERRDLPPNLYIRNNGYYCYRDPRTGKEFGLGRDRRFAITEAIQANIELFSG
HKHKPLTARINSDNSVTLHSWLDRYEKILASRGIKQKTLINYMSKIKAIRRGLPDAPL
EDITTKEIAAMLNGYIDEGKAASAKLIRSTLSDAFREAIAEGHITTNHVAATRAAKSK
VRRSRLTADEYLKIYQAAESSPCWLRLAMELAVVTGQRVGDLCKMKWSDIVDGYLYVE
QSKTGVKIAIPTALHIDALGISMKETLDKCKEILGGETIIASTRREPLSSGTVSRYFM
RARKASGLSFEGDPPTFHELRSLSARLYGKQISDKFAQHLLGHKSVTMASQYRDDRGR
EWDKIEIK SEQ ID NO: 4
Lambda integrase:
ATGGGAAGAAGGCGAAGTCATGAGCGCCGGGATTTACCCCCTAACCTTTATATAAGAA
ACAATGGATATTACTGCTACAGGGACCCAAGGACGGGTAAAGAGTTTGGATTAGGCAG
AGACAGGCGAATCGCAATCACTGAAGCTATACAGGCCAACATTGAGTTATTTTCAGGA
CACAAACACAAGCCTCTGACAGCGAGAATCAACAGTGATAATTCCGTTACGTTACATT
CATGGCTTGATCGCTACGAAAAAATCCTGGCCAGCAGAGGAATCAAGCAGAAGACACT
CATAAATTACATGAGCAAAATTAAAGCAATAAGGAGGGGTCTGCCTGATGCTCCACTT
GAAGACATCACCACAAAAGAAATTGCGGCAATGCTCAATGGATACATAGACGAGGGCA
AGGCGGCGTCAGCCAAGTTAATCAGATCAACACTGAGCGATGCATTCCGAGAGGCAAT
AGCTGAAGGCCATATAACAACAAACCATGTCGCTGCCACTCGCGCAGCAAAATCAAAG
GTAAGGAGATCAAGACTTACGGCTGACGAATACCTGAAAATTTATCAAGCAGCAGAAT
CATCACCATGTTGGCTCAGACTTGCAATGGAACTGGCTGTTGTTACCGGGCAACGAGT
TGGTGATTTATGCAAAATGAAGTGGTCTGATATCGTAGATGGATATCTTTATGTCGAG
CAAAGCAAAACAGGCGTAAAAATTGCCATCCCAACAGCATTGCATATTGATGCTCTCG
GAATATCAATGAAGGAAACACTTGATAAATGCAAAGAGATTCTTGGCGGAGAAACCAT
AATTGCATCTACTCGTCGCGAACCGCTTTCATCCGGCACAGTATCAAGGTATTTTATG
CGCGCACGAAAAGCATCAGGTCTTTCCTTCGAAGGGGATCCGCCTACCTTTCACGAGT
TGCGCAGTTTGTCTGCAAGACTCTATGAGAAGCAGATAAGCGATAAGTTTGCTCAACA
TCTTCTCGGGCATAAGTCGGACACCATGGCATCACAGTATCGTGATGACAGAGGCAGG
GAGTGGGACAAAATTGAAATCAAATAA

SEQ ID NO: 5

-continued

| Materials |
|---|

attB: CTGCTTTTTT ATACTAACTT G

SEQ ID NO: 6
attP: CAGCTTTTTT ATACTAAGTT G

SEQ ID NO: 7
attH: CTGCTTTCTT ATACCAAGTG G

SEQ ID NO: 8
attPH: CAGCTTTCTT ATACCAAGTT G

SEQ ID NO: 9
attP4X: CAGCTTTATT TCATTAAGTT G

SEQ ID NO: 10
petF2: CATCGGTGATGTCGGCGAT

SEQ ID NO: 11
petR: CGGATATAGTTCCTCCTTTCAGCA

SEQ ID NO: 12
attP-F: cacagaattcCGT CTG TTA CAG GTC ACT AAT ACC ATC T

SEQ ID NO: 13
attPSOE-R: ACA TTT CCC CGA AAA GTG CCA CCT GAA CAT CAC CGG
GAA ATC AAA TAA TGA T SEQ ID NO: 14
TEM1prom-F: TTC AGG TGG CAC TTT TCG GGG AAA TGT SEQ ID NO: 15
TEM1prom-R: TGT GGA ATT CCT ACA CTA GAA GGA CAG TAT TTG
GTA TCT GC SEQ ID NO: 16
EcoliAttB-F: CTG AAA ATG TGT TCA CAG GTT GCT SEQ ID NO: 17
EcoliattB-R: GCA ATG CCA TCT GGT ATC ACT SEQ ID NO: 18
C2 gene sequence:
ATGGGAAGAAGGCGAAGTCATGAGCGCCGGGATTTACCCCCTAACCTTTATATAAGAA
ACAATGGATATTACTGCTACAGGGACCCAAGGACGGGTAAAGAGTTTGGATTAGGCAG
AGACAGGCGAATCGCAATCACTGAAGCTATACAGGCCAACATTGAGTTATTTTCAGGA
CACAAACACAAGCCTCTGACAGCGAGAATCAACAGTGATAATTCCGTTACGTTACATT
CATGGCTTGATCGCTACGAAAAAATCCTGGCCAGCAGAGGAATCAAGCAGAAGACACT
CATAAATTACATGAGCAAAATTAAAGCAATAAGGAGGGGTCTGCCTGATGCTCCACTT
GAAGACATCACCACAAAAGAAATTGCGGCAATGCTCAATGGATACATAGACGAGGGCA
AGGCGGCGTCAGCCAAGTTAATCAGATCAACGCTGAGCGATGCATTCCGAGAGGCAAT
AGCTGAAGGCCATATAACAACAAACCATGTCGCTGCCACTCGCGCAGCAAAGTCAAAG
GTAAGGAGATCAAGACTTACGGCTGACGAATACCTGAAAATTTATCAAGCAGCAGAAT
CATCACCATGTTGGCTCAGACTTGCAATGGAACTGGCTGTTGTTACCGGGCAACGAGT
TGGTGACTTGTGCAAAATGAAGTGGTCTGATATCGTAGATGGATATCTTTATGTCGAG
CAAAGCAAAACAGGCGTAAAAATTGCCATCCCAACAGCATTGCATATTGATGCTCTCG
GAATATCAATGAAGGAAACACTTGATAAATGCAAAGAGATTCTTGGCGGAGAAACCAT
AATTGCATCTACTCGTCGCGAACCGCTTTCATCCGGCACAGTATCAAGGTATTTTATG
CGCGCACGAAAAGCATCAGGTCTTTCCTTCGAAGGGGATCCGCCTACCTTTCACGAGT
TGCGCAGTTTGTCTGCAAGACTCTATGAGAAGCAGATAAGCGATAAGTTTGCTCAACA
TCTTCTCGGGCATAAGTCGGTCACCATGGCATCACAGTATCGTGATGACAGAGGCAGG
GAGTGGGACAAAATTGAAATCAAATAA SEQ ID NO: 19
C3 gene sequence:
ATGGGAAGAAGGCGAAGTCATGAGCGCCGGGATTTACCCCCTAACCTTTATATAAGAA
ACAATGGATATTACTGCTACAGGGACCCAAGGACGGGTAAAGAGTTTGGATTAGGCAG
AGACAGGCGATTCGCAATCACTGAAGCTATACAGGCCAACATTGAGTTATTTTCAGGA
CACAAACACAAGCCTCTGACAGCGAGAATCAACAGTGATAATTCCGTTACGTTACATT
CATGGCTTGATCGCTACGAAAAAATCCTGGCCAGCAGAGGAATCAAGCAGAAGACACT
CATAAATTACATGAGCAAAATTAAAGCAATAAGGAGGGGTCTGCCTGATGCTCCACTT
GAAGACATCACCACAAAAGAAATTGCGGCAATGCTCAATGGATACATAGACGAGGGCA
AGGCGGCGTCAGCCAAGTTAATCAGATCAACGCTGAGCGATGCATTCCGAGAGGCAAT
AGCTGAAGGCCATATAACAACAAACCATGTCGCTGCCACTCGCGCGGCAAAGTCAAAG
GTAAGGAGATCAAGACTTACGGCTGACGAATACCTGAAAATTTATCAAGCAGCAGAAT
CATCACCATGTTGGCTCAGACTTGCAATGGAACTGGCTGTTGTTACCGGGCAACGAGT
TGGTGACTTGTGCAAAATGAAGTGGTCTGATATCGTAGATGGATATCTTTATGTCGAG
CAAAGCAAAACAGGCGTAAAAATTGCCATCCCAACAGCATTGCATATTGATGCTCTCG -continued

| Materials |
|---|
| GAATATCAATGAAGGAAACACTTGATAAATGCAAAGAGATTCTTGGCGGAGAAACCAT<br>AATTGCATCTACTCGTCGCGAACCGCTCTCATCCGGCACAGTATCAAGGTATTTTATG<br>CGCGCACGAAAAGCATCAGGTCTTTCCTTCGAAGGGGATCCGCCTACCTTTCACGAGT<br>TGCGCAGTTTGTCTGCAAGACTCTATGGGAAGCAGATAAGCGATAAGTTTGCTCAACA<br>TCTTCTCGGGCATAAGTCGGTCACCATGGCATCACAGTATCGTGATGACAGAGGCAGG<br>GAGTGGGACAAAATTGAAATCAAATAA |
| SEQ ID NO: 20<br>C3 minicircle:<br>CATCGGTGATGTCGGCGATATAGGCGCCAGCAACCGCACCTGTGGCGCCGGTGATGCC<br>GGCCACGATGCGTCCGGCGTAGAGGATCGAGATCTCGATCCCGCGAAATTAATACGAC<br>TCACTATAGGGGAATTGTGAGCGGATAACAATTCCCCTCTAGAAATAATTTTGTTTAA<br>CTTTAAGAAGGAGATATACATATGGGAAGAAGGCGAAGTCATGAGCGCCGGGATTTAC<br>CCCCTAACCTTTATATAAGAAACAATGGATATTACTGCTACAGGGACCCAAGGACGGG<br>TAAAGAGTTTGGATTAGGCAGAGACAGGCGATTCGCAATCACTGAAGCTATACAGGCC<br>AACATTGAGTTATTTTCAGGACACAAACACAAGCCTCTGACAGCGAGAATCAACAGTG<br>ATAATTCCGTTACGTTACATTCATGGCTTGATCGCTACGAAAAAATCCTGGCCAGCAG<br>AGGAATCAAGCAGAAGACACTCATAAATTACATGAGCAAAATTAAAGCAATAAGGAGG<br>GGTCTGCCTGATGCTCCACTTGAAGACATCACCACAAAAGAAATTGCGGCAATGCTCA<br>ATGGATACATAGACGAGGGCAAGGCGGCGTCAGCCAAGTTAATCAGATCAACGCTGAG<br>CGATGCATTCCGAGAGGCAATAGCTGAAGGCCATATAACAACAAACCATGTCGCTGCC<br>ACTCGCGCGGCAAAGTCAAAGGTAAGGAGATCAAGACTTACGGCTGACGAATACCTGA<br>AAATTTATCAAGCAGCAGAATCATCACCATGTTGGCTCAGACTTGCAATGGAACTGGC<br>TGTTGTTACCGGGCAACGAGTTGGTGACTTGTGCAAAATGAAGTGGTCTGATATCGTA<br>GATGGATATCTTTATGTCGAGCAAAGCAAAACAGGCGTAAAAATTGCCATCCCAACAG<br>CATTGCATATTGATGCTCTCGGAATATCAATGAAGGAAACACTTGATAAATGCAAAGA<br>GATTCTTGGCGGAGAAACCATAATTGCATCTACTCGTCGCGAACCGCTCTCATCCGGC<br>ACAGTATCAAGGTATTTTATGCGCGCACGAAAAGCATCAGGTCTTTCCTTCGAAGGGG<br>ATCCGCCTACCTTTCACGAGTTGCGCAGTTTGTCTGCAAGACTCTATGGGAAGCAGAT<br>AAGCGATAAGTTTGCTCAACATCTTCTCGGGCATAAGTCGGTCACCATGGCATCACAG<br>TATCGTGATGACAGAGGCAGGGAGTGGGACAAAATTGAAATCAAACATCATCACCATC<br>ACCACTAATGAGAATTCgagctccgtcgacaagcttgcggccgcactcgagcaccacc<br>accaccaccactgagatccggctgctaacaaagcccgaaaggaagctgagttggctgc<br>tgccaccgctgagcaataactagcataaccccttggggcctctaaacgggtcttgagg<br>ggtttttttgctgaaaggaggaactatatccg |
| SEQ ID NO: 21<br>attP-TEM1:<br>cacagaattcCGtctgttacaggtcactaataccatctaagtagttgattcatagtga<br>ctgcatatattgtgttttacagtattatgtagtctgtttttttatgcaaaatctaattt<br>aatatattgatatttatatcattttacgtttctcgttcagctttttttatactaagttg<br>gcattataaaaaagcattgcttatcaatttgttgcaacgaacaggtcactatcagtca<br>aaataaaatcattatttgATTTCCCGGTGATGttcaggtggcacttttcggggaaatg<br>tgcgcggaacccctatttgtttatttttctaaatacattcaaatatgtatccgctcat<br>gagacaataaccctgataaatgcttcaataatattgaaaaaggaagagtatgagtatt<br>caacatttccgtgtcgcccttattcccttttttgcggcattttgccttcctgtttttg<br>ctcacccagaaacgctggtgaaagtaaaagatgctgaagatcagttgggtgcacgagt<br>gggttacatcgaactggatctcaacagcggtaagatccttgagagttttcgccccgaa<br>gaacgttttccaatgatgagcacttttaaagttctgctatgtggcgcggtattatccc<br>gtattgacgccgggcaagagcaactcggtcgccgcatacactattctcagaatgactt<br>ggttgagtactcaccagtcacagaaaagcatcttacggatggcatgacagtaagagaa<br>ttatgcagtgctgccataaccatgagtgataacactgcggccaacttacttctgacaa<br>cgatcggaggaccgaaggagctaaccgcttttttgcacaacatgggggatcatgtaac<br>tcgccttgatcgttgggaaccggagctgaatgaagccataccaaacgacgagcgtgac<br>accacgatgcctgcagcaatggcaacaacgttgcgcaaactattaactggcgaactac<br>ttactctagcttcccggcaacaattaatagactggatggaggcggataaagttgcagg<br>accacttctgcgctcggcccttccggctggctggtttattgctgataaatctggagcc<br>ggtgagcgtgggtctcgcggtatcattgcagcactggggccagatggtaagccctccc<br>gtatcgtagttatctacacgacggggagtcaggcaactatggatgaacgaaatagaca<br>gatcgctgagataggtgcctcactgattaagcattggtaactgtcagaccaagtttac<br>tcatatatactttagattgatttaaaacttcatttttaatttaaaaggatctaggtga<br>agatcctttttgataatctcatgaccaaaatcccttaacgtgagttttcgttccactg<br>agcgtcagaccccgtagaaaagatcaaaggatcttcttgagatcctttttttctgcgc<br>gtaatctgctgcttgcaaacaaaaaaaccaccgctaccagcggtggtttgtttgccgg<br>atcaagagctaccaactctttttccgaaggtaactggcttcagcagagcgcagatacc<br>aaatactgtccttctagtgtagccgtagttagg |
| SEQ ID NO: 22<br>HOP': ATGCTTTATTTCATTAAGTTG |
| SEQ ID NO: 23<br>attL: GCATTATAAAAAAGCATTGCTTATCAATTTGTTGCAACGAACAGGTCACTATC<br>AGTCAAAATACAATCATTATTTGATTTCAATTTTGTCCCACTCCCTCCCG |
| SEQ ID NO: 24<br>PGK promoter:<br>AATTCTACCGGGTAGGGGAGGCGCTTTTCCCAAGGCAGTCTGGAGCATGCGCTTTAGC |

-continued

| Materials |
| --- |

AGCCCCGCTGGGCACTTGGCGCTACACAAGTGGCCTCTGGCCTCGCACACATTCCACA
TCCACCGGTAGGCGCCAACCGGCTCCGTTCTTTGGTGGCCCCTTCGCGCCACCTTCTA
CTCCTCCCCTAGTCAGGAAGTTCCCCCCCGCCCCGCAGCTCGCGTCGTGCAGGACGTG
ACAAATGGAAGTAGCACGTCTCACTAGTCTCGTGCAGATGGACAGCACCGCTGAGCAA
TGGAAGCGGGTAGGCCTTTGGGGCAGCGGCCAATAGCAGCT

SEQ ID NO: 25
HOP' attH4X_F1: GAGTGTTTTCCAACTTGGTTCCATT

SEQ ID NO: 26
PuroRev24: CACCGTGGGCTTGTACTCGGTC

SEQ ID NO: 27
pLIR-F1: CTGCATCGATTCAGCTAGCTG

SEQ ID NO: 28
pLIR-R1: CTGATAGTGACCTGTTCGTTGC

SEQ ID NO: 29
pPGKssPuro-attP4x (targeting vector):
gaattcctctgttacaggtcactaataccatctaagtagttgattcatagtgactgca
tatgttgtgttttacagtattatgtagtctgtttttatgcaaaatctaatttaatat
attgatatttatatcattttacgtttctcgttcagctttatttcattaagttggcatt
ataaaaaagcattgcttatcaatttgttgcaacgaacaggtcactatcagtcaaaata
aaatcattatttgatttcaattttgtcccactccctcccgaattctaccgggtagggg
aggcgcttttcccaaggcagtctggagcatgcgctttagcagccccgctggcacttgg
cgctacacaagtggcctctggcctcgcacacattccacatccaccggtagcgccaacc
ggctccgttctttggtggccccttcgcgccacttctactcctcccctagtcaggaagt
tcccccccgccccgcagctcgcgtcgtgcaggacgtgacaaatggaagtagcacgtc
tcactagtctcgtgcagatggacagcaccgctgagcaatggaagcgggtaggcctttg
gggcagcggccaatagcagctttgctccttcgctttctgggctcagaggctgggaagg
ggtgggtccgggggcgggctcaggggcgggctcaggggcggggcgggcgcccgaaggt
cctccggaggcccggcattctgcacgcttcaaaagcgcacgtctgccgcgctgttctc
ctcttcctcatctccgggcctttcgaccaattcgctgtctgcgagggccagctgttgg
ggtgagtactccctctcaaaagcgggcatgacttctgcgctaagattgtcagtttcca
aaaacgaggaggatttgatattcacctggcccgcggtgatgcctttgagggtggccgc
gtccatctggtcagaaaagacaatctttttgttgtcaagcttgaggtgtggcaggctt
gagatctggccatacacttgagtgacaatgacatccactttgcctttctctccacagg
tgtccactcccaggtccaactgcagatgaccgagtacaagcccacggtgcgcctcgcc
acccgcgacgacgtcccccgggccgtacgcaccctcgccgccgcgttcgccgactacc
ccgccacgcgccacaccgtcgacccggaccgccacatcgagcgggtcaccgagctgca
agaactcttcctcacgcgcgtcgggctcgacatcggcaaggtgtgggtcgcggacgac
ggcgccgcggtggcggtctggaccacgccggagagcgtcgaagcgggggcggtgttcg
ccgagatcggcccgcgcatggccgagttgagcggttcccggctggccgcgcagcaaca
gatggaaggcctcctggcgccgcaccggcccaaggagcccgcgtggttcctggccacc
gtcggcgtctcgcccgaccaccagggcaagggtctgggcagcgccgtcgtgctccccg
gagtggaggcggccgagcgcgccggggtgcccgccttcctggagacctccgcgccccg
caacctccccttctacgagcggctcggcttcaccgtcaccgccgacgtcgaggtgccc
gaaggaccgcgcacctggtgcatgacccgcaagcccggtgcctgatctagagctcgct
gatcagcctcgactgtgccttctagttgccagccatctgttgtttgcccctcccccgt
gccttccttgaccctggaaggtgccactcccactgtcctttcctaataaaatgaggaa
attgcatcgcattgtctgagtaggtgtcattctattctggggggtggggtggggcagg
acagcaagggggaggattgggaagacaatagcaggcatgctggggatgcggtgggctc
tatggcttctgaggcggaaagaaccagctggggctcgagatccactagttctagcctc
gaggctagagcggccgccaccgcggtggagctccaattcgccctatagtgagtcgtat
tacgcgcgctcactggccgtcgttttacaacgtcgtgactgggaaaaccctggcgtta
cccaacttaatcgccttgcagcacatccccctttcgccagctggcgtaatagcgaaga
ggcccgcaccgatcgcccttcccaacagttgcgcagcctgaatggcgaatgggacgcg
ccctgtagcggcgcattaagcgcggcgggtgtggtggttacgcgcagcgtgaccgcta
cacttgccagcgccctagcgcccgctcctttcgctttcttcccttcctttctcgccac
gttcgccggctttccccgtcaagctctaaatcgggggctccctttagggttccgattt
agtgctttacggcacctcgaccccaaaaaacttgattagggtgatggttcacgtagtg
ggccatcgccctgatagacggtttttcgccctttgacgttggagtccacgttctttaa
tagtggactcttgttccaaactggaacaacactcaaccctatctcggtctattctttt
gatttataagggattttgccgatttcggcctattggttaaaaaatgagctgatttaac
aaaaatttaacgcgaattttaacaaaatattaacgcttacaatttaggtggcactttt
cggggaaatgtgcgcggaacccctatttgtttatttttctaaatacattcaaatatgt
atccgctcatgagacaataaccctgataaatgcttcaataatattgaaaaaggaagag
tatgagtattcaacatttccgtgtcgcccttattcccttttttgcggcattttgcctt
cctgtttttgctcacccagaaacgctggtgaaagtaaaagatgctgaagatcagttgg
gtgcacgagtgggttacatcgaactggatctcaacagcggtaagatccttgagagttt
tcgccccgaagaacgttttccaatgatgagcacttttaaagttctgctatgtggcgcg
gtattatcccgtattgacgccgggcaagagcaactcggtcgccgcatacactattctc
agaatgacttggttgagtactcaccagtcacagaaaagcatcttacggatggcatgac
agtaagagaattatgcagtgctgccataaccatgagtgataacactgcggccaactta
cttctgacaacgatcggaggaccgaaggagctaaccgcttttttgcacaacatgggg
atcatgtaactcgccttgatcgttgggaaccggagctgaatgaagccataccaaacga -continued

| Materials |
| --- |
| cgagcgtgacaccacgatgcctgtagcaatggcaacaacgttgcgcaaactattaact |
| ggcgaactacttactctagcttcccggcaacaattaatagactggatggaggcggata |
| aagttgcaggaccacttctgcgctcggcccttccggctggctggtttattgctgataa |
| atctggagccggtgagcgtgggtctcgcggtatcattgcagcactggggccagatggt |
| aagccctcccgtatcgtagttatctacacgacggggagtcaggcaactatggatgaac |
| gaaatagacagatcgctgagataggtgcctcactgattaagcattggtaactgtcaga |
| ccaagtttactcatatatactttagattgatttaaaacttcatttttaatttaaaagg |
| atctaggtgaagatcctttttgataatctcatgaccaaaatcccttaacgtgagtttt |
| cgttccactgagcgtcagaccccgtagaaaagatcaaaggatcttcttgagatccttt |
| ttttctgcgcgtaatctgctgcttgcaaacaaaaaaaccaccgctaccagcggtggtt |
| tgtttgccggatcaagagctaccaactctttttccgaaggtaactggcttcagcagag |
| cgcagataccaaatactgtccttctagtgtagccgtagttaggccaccacttcaagaa |
| ctctgtagcaccgcctacatacctcgctctgctaatcctgttaccagtggctgctgcc |
| agtggcgataagtcgtgtcttaccgggttggactcaagacgatagttaccggataagg |
| cgcagcggtcgggctgaacggggggttcgtgcacacagcccagcttggagcgaacgac |
| ctacaccgaactgagatacctacagcgtgagctatgagaaagcgccacgcttcccgaa |
| gggagaaaggcggacaggtatccggtaagcggcagggtcggaacaggagagcgcacga |
| gggagcttccagggggaaacgcctggtatctttatagtcctgtcgggtttcgccacct |
| ctgacttgagcgtcgatttttgtgatgctcgtcaggggggcggagcctatggaaaaac |
| gccagcaacgcggcctttttacggttcctggccttttgctggccttttgctcacatgt |
| tctttcctgcgttatcccctgattctgtggataaccgtattaccgcctttgagtgagc |
| tgataccgctcgccgcagccgaacgaccgagcgcagcgagtcagtgagcgaggaagcg |
| gaagagcgcccaatacgcaaaccgcctctccccgcgcgttggccgattcattaatgca |
| gctggcacgacaggtttcccgactggaaagcgggcagtgagcgcaacgcaattaatgt |
| gagttagctcactcattaggcaccccaggctttacactttatgcttccggctcgtatg |
| ttgtgtggaattgtgagcggataacaatttcacacaggaaacagctatgaccatgatt |
| acgccaagcgcgcaattaaccctcactaaagggaacaaaagctgggtaccgggccccc |
| cctcgaggtcgacggtatcgataagcttgatatc |
| |
| SEQ ID NO: 30 |
| pCMVssKZ-IntC3-CNLS (the integrase expression plasmid): |
| gaattcctcacatgttctttcctgcgttatcccctgattctgtggataaccgtattac |
| cgccatgcattagttattaatagtaatcaattacggggtcattagttcatagcccata |
| tatggagttccgcgttacataacttacggtaaatggcccgcctggctgaccgcccaac |
| gacccccgcccattgacgtcaataatgacgtatgttcccatagtaacgccaataggga |
| ctttccattgacgtcaatgggtggagtatttacggtaaactgcccacttggcagtaca |
| tcaagtgtatcatatgccaagtacgccccctattgacgtcaatgacggtaaatggccc |
| gcctggcattatgcccagtacatgaccttatgggactttcctacttggcagtacatct |
| acgtattagtcatcgctattaccatggtgatgcggttttggcagtacatcaatgggcg |
| tggatagcggtttgactcacggggatttccaagtctccaccccattgacgtcaatggg |
| agtttgttttggcaccaaaatcaacgggactttccaaaatgtcgtaacaactccgccc |
| cattgacgcaaatgggcggtaggcgtgtacggtgggaggtctatataagcagagctgg |
| tttagtgaaccgtcagatccgctagcaattcgctgtctgcgagggccagctgttgggg |
| tgagtactccctctcaaaagcgggcatgacttctgcgctaagattgtcagtttccaaa |
| aacgaggaggatttgatattcacctggcccgcggtgatgcctttgagggtggccgcgt |
| ccatctggtcagaaaagacaatctttttgttgtcaagcttgaggtgtggcaggcttga |
| gatctggccatacacttgagtgacaatgacatccactttgcctttctctccacaggtg |
| tccactcccaggtccaactgcagctcgaggtccaccatgggaagaaggcgaagtcatg |
| agcgccgggatttacccccctaacctttatataagaaacaatggatattactgctacag |
| ggacccaaggacgggtaaagagtttggattaggcagagacaggcgattcgcaatcact |
| gaagctatacaggccaacattgagttattttcaggacacaaacacaagcctctgacag |
| cgagaatcaacagtgataattccgttacgttacattcatggcttgatcgctacgaaaa |
| aatcctggccagcagaggaatcaagcagaagacactcataaattacatgagcaaaatt |
| aaagcaataaggaggggtctgcctgatgctccacttgaagacatcaccacaaaagaaa |
| ttgcggcaatgctcaatggatacatagacgagggcaaggcggcgtcagccaagttaat |
| cagatcaacgctgagcgatgcattccgagaggcaatagctgaaggccatataacaaca |
| aaccatgtcgctgccactcgcgcggcaaagtcaaaggtaaggagatcaagacttacgg |
| ctgacgaatacctgaaaatttatcaagcagcagaatcatcaccatgttggctcagact |
| tgcaatggaactggctgttgttaccgggcaacgagttggtgacttgtgcaaaatgaag |
| tggtctgatatcgtagatggatatctttatgtcgagcaaagcaaaacaggcgtaaaaa |
| ttgccatcccaacagcattgcatattgatgctctcggaatatcaatgaaggaaacact |
| tgataaatgcaaagagattcttggcggagaaaccataattgcatctactcgtcgcgaa |
| ccgctctcatccggcacagtatcaaggtattttatgcgcgcacgaaaagcatcaggtc |
| tttccttcgaaggggatccgcctacctttcacgagttgcgcagtttgtctgcaagact |
| ctatgggaagcagataagcgataagtttgctcaacatcttctcgggcataagtcggtc |
| accatggcatcacagtatcgtgatgacagaggcagggagtgggacaaaattgaaatca |
| aatccggaggcggccctaagaagaagagaaaggtatgataatctagagctcgctgatc |
| agcctcgactgtgccttctagttgccagccatctgttgtttgcccctcccccgtgcct |
| tccttgaccctggaaggtgccactcccactgtcctttcctaataaaatgaggaaattg |
| catcgcattgtctgagtaggtgtcattctattctggggggtggggtggggcaggacag |
| caagggggaggattgggaagacaatagcaggcatgctggggatgcggtgggctctatg |
| gcttctgaggcggaaagaaccagctggggctcgagatccactagttctagcctcgagg |
| ctagagcggccgccaccgcggtggagctccaattcgccctatagtgagtcgtattacg |
| cgcgctcactggccgtcgttttacaacgtcgtgactgggaaaaccctggcgttaccca |
| acttaatcgccttgcagcacatccccctttcgccagctggcgtaatagcgaagaggcc |
| cgcaccgatcgcccttcccaacagttgcgcagcctgaatggcgaatggacgcgccct |
| gtagcggcgcattaagcgcggcgggtgtggtggttacgcgcagcgtgaccgctacact |

-continued

| Materials |
| --- |
| tgccagcgccctagcgcccgctcctttcgctttcttcccttcctttctcgccacgttc<br>gccggctttccccgtcaagctctaaatcgggggctccctttagggttccgatttagtg<br>ctttacggcacctcgaccccaaaaaacttgattagggtgatggttcacgtagtgggcc<br>atcgccctgatagacggtttttcgccctttgacgttggagtccacgttctttaatagt<br>ggactcttgttccaaactggaacaacactcaaccctatctcggtctattcttttgatt<br>tataagggattttgccgatttcggcctattggttaaaaaatgagctgatttaacaaaa<br>atttaacgcgaattttaacaaaatattaacgcttacaatttaggtggcacttttcggg<br>gaaatgtgcgcggaacccctatttgtttatttttctaaatacattcaaatatgtatcc<br>gctcatgagacaataaccctgataaatgcttcaataatattgaaaaaggaagagtatg<br>agtattcaacatttccgtgtcgcccttattcccttttttgcggcattttgccttcctg<br>tttttgctcacccagaaacgctggtgaaagtaaaagatgctgaagatcagttgggtgc<br>acgagtgggttacatcgaactggatctcaacagcggtaagatccttgagagttttcgc<br>cccgaagaacgttttccaatgatgagcacttttaaagttctgctatgtggcgcggtat<br>tatcccgtattgacgccgggcaagagcaactcggtcgccgcatacactattctcagaa<br>tgacttggttgagtactcaccagtcacagaaaagcatcttacggatggcatgacagta<br>agagaattatgcagtgctgccataaccatgagtgataacactgcggccaacttacttc<br>tgacaacgatcggaggaccgaaggagctaaccgcttttttgcacaacatgggggatca<br>tgtaactcgccttgatcgttgggaaccggagctgaatgaagccataccaaacgacgag<br>cgtgacaccacgatgcctgtagcaatggcaacaacgttgcgcaaactattaactggcg<br>aactacttactctagcttcccggcaacaattaatagactggatggaggcggataaagt<br>tgcaggaccacttctgcgctcggcccttccggctggctggtttattgctgataaatct<br>ggagccggtgagcgtgggtctcgcggtatcattgcagcactggggccagatggtaagc<br>cctcccgtatcgtagttatctacacgacggggagtcaggcaactatggatgaacgaaa<br>tagacagatcgctgagataggtgcctcactgattaagcattggtaactgtcagaccaa<br>gtttactcatatatactttagattgatttaaaacttcatttttaatttaaaaggatct<br>aggtgaagatcctttttgataatctcatgaccaaaatcccttaacgtgagttttcgtt<br>ccactgagcgtcagaccccgtagaaaagatcaaaggatcttcttgagatcctttttt<br>ctgcgcgtaatctgctgcttgcaaacaaaaaaaccaccgctaccagcggtggtttgtt<br>tgccggatcaagagctaccaactctttttccgaaggtaactggcttcagcagagcgca<br>gataccaaatactgtccttctagtgtagccgtagttaggccaccacttcaagaactct<br>gtagcaccgcctacatacctcgctctgctaatcctgttaccagtggctgctgccagtg<br>gcgataagtcgtgtcttaccgggttggactcaagacgatagttaccggataaggcgca<br>gcggtcgggctgaacggggggttcgtgcacacagcccagcttggagcgaacgacctac<br>accgaactgagatacctacagcgtgagctatgagaaagcgccacgcttcccgaaggga<br>gaaaggcggacaggtatccggtaagcggcagggtcggaacaggagagcgcacgaggga<br>gcttccagggggaaacgcctggtatctttatagtcctgtcgggtttcgccacctctga<br>cttgagcgtcgatttttgtgatgctcgtcaggggggcggagcctatggaaaaacgcca<br>gcaacgcggcctttttacggttcctggccttttgctggccttttgctcacatgttctt<br>tcctgcgttatcccctgattctgtggataaccgtattaccgcctttgagtgagctgat<br>accgctcgccgcagccgaacgaccgagcgcagcgagtcagtgagcgaggaagcggaag<br>agcgcccaatacgcaaaccgcctctccccgcgcgttggccgattcattaatgcagctg<br>gcacgacaggtttcccgactggaaagcgggcagtgagcgcaacgcaattaatgtgagt<br>tagctcactcattaggcaccccaggctttacactttatgcttccggctcgtatgttgt<br>gtggaattgtgagcggataacaatttcacacaggaaacagctatgaccatgattacgc<br>caagcgcgcaattaaccctcactaaagggaacaaaagctgggtaccgggccccccctc<br>gaggtcgacggtatcgataagcttgatatc |
| SEQ ID NO: 31<br>attH4X: acgctttatttcattaagttg |

Example 1

Rapid *E. coli* Chromosomal Integration

The present example follows the methodology depicted in FIG. 2. C3INT-HIS-PET22b(+) was amplified with petF2 (SEQ ID NO: 10) and petR (SEQ ID NO: 11) and the PCR product subsequently intramolecularly ligated to produce a C3INT-HIS minicircle. attP-PET22b(+) was amplified with attP-F (SEQ ID NO: 12) and attPSOE-R (SEQ ID NO: 13) while PET22b(+) was amplified with TEM1prom-F (SEQ ID NO: 14) and TEM1promR (SEQ ID NO: 15) which produced PCR products encoding attP and ampicillin-resistant gene respectively. Splice overlap extension PCR (SOE-PCR) was carried out with these two PCR products using attP-F (SEQ ID NO: 12) and TEM1prom-R (SEQ ID NO: 15). The PCR product was subsequently intramolecularly ligated to produce attP-TEM1 minicircle. 100 ng of C3INT-HIS minicircle and 100 ng attP-TEM1 minicircle were combined and electroporated to 25 μL electrocompetent TG1 cells. The cells were allowed to recover for 1 hr before being plated on varying concentrations of ampicillin-LB agar plates (0.01 mg/mL, 0.02 mg/mL, 0.05 mg/mL, 0.07 mg/mL and 0.1 mg/mL). Incubation was carried out at 37° C. for 12-14 hrs to allow for expression of C3 integrase and chromosomal integration of the ampicillin-resistance cassette by C3 integrase. Colony PCR was carried out with EcoliAttB-F (SEQ ID NO: 16) and EcoliAttB-R (SEQ ID NO: 17), TEM1prom-F (SEQ ID NO: 14) and EcoliAttB-F (SEQ ID NO: 16), or TEM1prom-F (SEQ ID NO: 14) and EcoliAttB-R (SEQ ID NO: 17) to verify the presence of chromosomal integration of the ampicillin-resistance cassette. The PCR products were also sequenced with the same primers to confirm the results. The sequencing indicated a correct integration event into the chromosomal attB site (FIG. 3C).

Example 2

Recombination Activity of the Parental and Integrase Variants C2 and C3

Figure 4A:
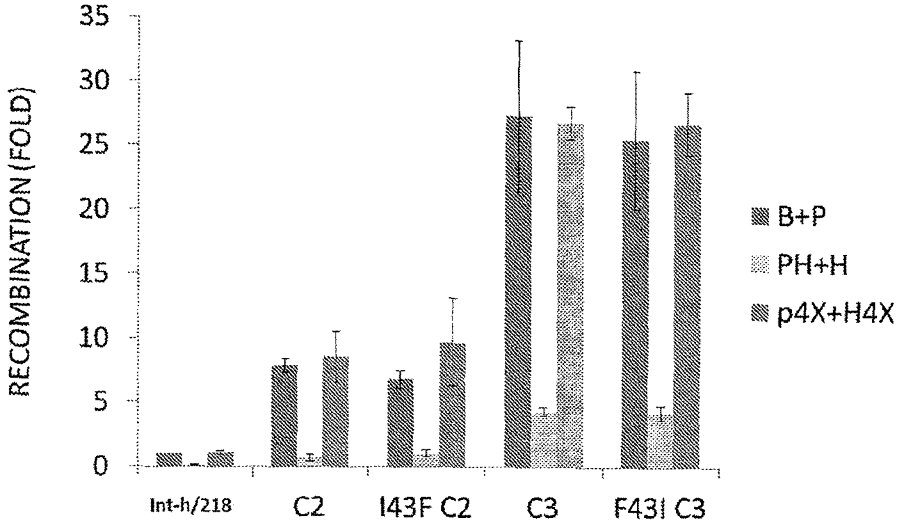
FIG. 4A shows the improved intramolecular recombination activity of parental Int-h/218 and indicated lambda integrase mutants expressed using an in vitro transcription/translation system for cognate (attB/attP) and non-cognate (attH/attPH and attH4x/attP4x) sites. Recombination is denoted relative to parental Int-h/218 efficiency with attB/P substrate (set to 1). Mutant lambda integrase proteins of the invention (C2 and C3) are more efficient at performing the respective recombination reactions. C2 denotes lambda integrase mutants with the D336V mutation. I43F C2 denotes the C2 lambda integrase mutants with an additional I43F mutation. C3 denotes lambda integrase mutants with the I43F, E319G, D336V mutations. N=2, bars indicate means+/−SD.

The present example demonstrates the recombination activity of the parental Int-h/218 and selected mutants (C2, C3 and indicated variants thereof). FIG. 4A depicts results from an in vitro intramolecular recombination reaction using integrases produced by in vitro transcription/translation. Plasmids encoding the respective integrase (Int-h/218, C2,C3 or variant thereof) were amplified using primers IntRBS-F and INTstop-R, and the PCR products re-amplified with primers Univeral and INTstop-R to get integrase amplicons with T7 promoter and ribosome binding site required for in vitro transcription-translation (IVT). 20 ng of each integrase amplicon was expressed using PURExpress® In Vitro Protein Synthesis Kit in a total volume of 9 μL at 30° C. for 1 hour. Intramolecular recombination was then carried out by adding 10 ng plasmid substrate containing either attB/attP sites, attPH/attH sites or attH4x/attP4x sites (FIG. 1) to a total volume of 10 μL. The mixture was allowed to incubate for 2 hours at 37° C. The reaction was subsequently diluted 1/10 before taking 1 μL for real-time PCR quantification of recombination efficiency. Real-time PCR quantification was carried out with 250 nM each of primers pLIR-F1 (SEQ ID NO: 27) and pLIR-R1 (SEQ ID NO: 28) in a final volume of 20 μL with SsoAdvanced™ Universal SYBR® Green Supermix. The activities of the recombinant integrase proteins are presented relative to activity of WT Int-h/218 on attB/attP plasmid substrate (set as value of 1). Error bars indicate standard deviation of two independent experiments.

The results show significant increases in recombination efficiency for the C2 and C3 integrases compared to parental Int-h/218. The data in FIG. 4 show the strong contribution of the E319G mutation present in C3 on the efficiency of intramolecular recombination. Removing this mutation from C3 yields I43F C2 which shows ~3 fold reduced activity on all substrate pairs tested. The contribution of the I43F mutation for intramolecular recombination is not readily apparent, as addition of this to C2 or removal from C3 does not lead to any significant change in recombination efficiency. However, it could impact on other parameters such as intermolecular recombination in vivo and/or protein stability.

Figure 4B:
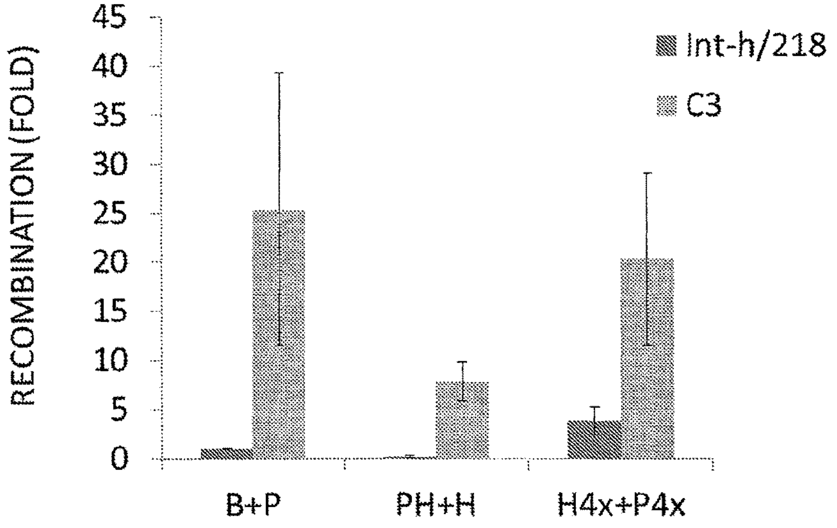
FIG. 4B shows intramolecular recombination activity of parental Int-h/218 and C3 integrase on indicated substrates. Intramolecular recombination was carried out with 5 μg of purified recombinant integrase protein incubated with 10 ng plasmid substrate containing either attB/attP sites, attH/attPH sites or attH4x/attP4x sites. The reaction volume was 25 μL and was carried out for 1.5 hours at 37° C. in recombination buffer (100 mM Tris pH7.5, 500 mM NaCl, 25 mM DTT, 10 mM EDTA, 5 mg/mL bovine serum albumin). The reaction was diluted 1/10 before taking 2 μL for real-time PCR quantification of recombination efficiency. Real-time PCR quantification was carried out with 250 nM each of primers pLIR-F1 (SEQ ID NO: 27) and pLIR-R1 (SEQ ID NO: 28) in a final volume of 20 μL with SsoAdvanced™ Universal SYBR® Green Supermix. The activities of the recombinant integrase proteins are presented relative to activity of Int-h/218 on attB/attP plasmid substrate (set as value of 1). Error bars indicate average +/−SD of 2 independent experiments.

FIG. 4B depicts results from in an vitro intramolecular recombination reaction using integrases produced recombinantly in *E. coli*. Plasmids expressing integrase Int-h/218 and C3 were transformed into *E. coli* BL21(DE3)pLysS (Invitrogen) competent cells. The bacterial cells were grown in LB medium at 37° C. and induced at $OD_{600\ nm}$ of ~0.6 with 0.5 mM IPTG at 30° C. for 6 hours. The cells were then harvested by centrifugation, resuspended in 50 mM Tris pH 8.0, 1M NaCl, 20 mM Imidazole and lysed by sonication. The cell lysate was clarified by high-speed centrifugation and the supernatant was then applied to a 1 mL HisTrap™ FF column (GE Healthcare) pre-equilibrated in binding buffer of 50 mM Tris-HCl pH 8.0, 1M NaCl, 20 mM Imidazole, 0.5 mM EDTA and 2 mM DTT. The column was washed with binding buffer and the integrase proteins were eluted off the column with 50 mM Tris-HCl pH 8.0, 1M NaCl, 500 mM Imidazole, 0.5 mM EDTA and 2 mM DTT. Collected fractions were analyzed by SDS-PAGE gel and the appropriate fractions were dialyzed and concentrated in 50 mM Tris pH 8.0, 1M NaCl, 0.5 mM EDTA and 2 mM DTT using Amicon-Ultra (10 kDa MWCO) prior to storage at −80° C.

Intramolecular recombination was carried out with 5 μg of purified recombinant integrase protein incubated with 10 ng plasmid substrate containing either attB/attP sites, attPH/attH sites or attH4x/attP4x sites. The reaction volume was 25 μL and was carried out for 1.5 hours at 37° C. in recombination buffer (100 mM Tris pH7.5, 500 mM NaCl, 25 mM DTT, 10 mM EDTA, 5 mg/mL bovine serum albumin). The reaction was diluted 1/10 before taking 2 μL for real-time PCR quantification of recombination efficiency. Real-time PCR quantification was carried out with 250 nM each of primers pLIR-F1 (SEQ ID NO: 27) and pLIR-R1 (SEQ ID NO: 28) in a final volume of 20 μL with SsoAdvanced™ Universal SYBR® Green Supermix. The activities of the recombinant integrase proteins are presented relative to activity of Int-h/218 (WT) on attB/attP plasmid substrate (set as value of 1). Error bars indicate average+/− SD of 2 independent experiments. The data again show increased recombination on all substrates tested for the C3 integrase compared to Int-h/218 parent.

The improved recombination activities of C2 and C3 observed in these experiments (FIGS. 4A and 4B) correlate with those seen in cell-based assays (FIG. 5).

Example 3

Cell Culture Conditions, Transfection Procedure and Selection of Puromycin-resistant Recombinants for Endogenous attH4x Targeting in HT1080 Cells For endogenous targeting in the HT1080 cell line, $3\times10^6$ cells were seeded in Dulbecco's Modified Eagle Medium [DMEM (Life technologies) supplemented with 10% FBS, 1% L-glutamine and 100 Units/mL of Penicillin and Streptomycin each] per 10 cm cell culture dish a day before transfection to obtain 70-90% confluence at the time of transfection. Transfections were done using Lipofectamine 2000 reagent (Life technologies). Plasmid DNA-Lipid complexes were prepared by mixing 5 ng of the targeting vector (pPGKssPuro-attP4x (SEQ ID NO: 29)) and 100 ng of the integrase expression plasmid (pCMVssKZ-IntC3-CNLS (SEQ ID NO: 30)) diluted in 75 μl of Opti-MEM medium with 2.5 μl of Lipofectamine 2000 reagent diluted in 75 μl of Opti-MEM medium (Life technologies) and incubating for 20 minutes at room temperature. The transfection mix was added onto the cells (under DMEM without antibiotics) and transfection was allowed to proceed for 4-6 hours following which the complexes were removed by replacing with fresh medium. 48 hours post-transfection, the cells were grown in growth medium containing 3 μg Puromycin per ml to select for puromycin-resistant colonies. After 3 weeks of selection, puromycin-resistant colonies were picked and expanded. Genomic DNA was extracted using DNeasy Blood & Tissue Kit (Qiagen).

Example 4

Cell Culture Conditions, Transfection Procedure and FACS Analysis for Episomal Intra-molecular Recombination Assay For the episomal intra-molecular recombination assays in HT1080 cell line, $3\times10^5$ cells were seeded in Dulbecco's Modified Eagle Medium [DMEM (Life technologies) supplemented with 10% FBS, 1% L-glutamine and 100 Units/mL of Penicillin and Streptomycin each] per well of 6 well plate a day before transfection to obtain 70-90% confluence at the time of transfection. Transfections were done using Lipofectamine 2000 reagent. For every transfection per well, plasmid DNA-Lipid complexes were prepared by mixing 1.5 μg of pLIR and 1.5 μg of the λ integrase expression plasmid diluted in 100 μl of Opti-MEM medium with 6 μl of Lipofectamine 2000 reagent diluted in 100 μl of Opti-MEM medium and incubating for 20 minutes at room temperature. The transfection mix was added dropwise onto the cells (under DMEM without antibiotics) and transfection was allowed to proceed for 4-6 hours following which the complexes were removed by replacing with fresh DMEM medium. 48-72 hours post-transfection, the cells were trypsinised and harvested with DMEM into eppendorf tubes, pelleted by centrifugation (at 1000×rcf for 5 minutes) and resuspended in 1 ml fresh DMEM. GFP positive cell were quantified by FACS on a BD FACSCalibur™ machine (Becton-Dickinson).

Example 5

Identifying Successful Sequence Specific Recombination Event

PCR was performed using GoTaq Flexi DNA polymerase (Promega) with primers HOP' attH4X_F1 (SEQ ID NO: 25) and PuroRev24 (SEQ ID NO: 26) and 200 ng of genomic DNA as template per PCR reaction in 50 μl volume. The following thermal cycling parameters were used for the PCR: an initial step of 95° C. for 5 minutes, 35 cycles of 95° C. for 1 minute, 57° C. for 30 seconds and 72° C. for 1 minute, and a final step of 72° C. for 5 minutes. The PCR samples were analyzed by electrophoresis in 0.8% agarose gel in Tris-Boric acid-EDTA buffer.

Figure 6A:
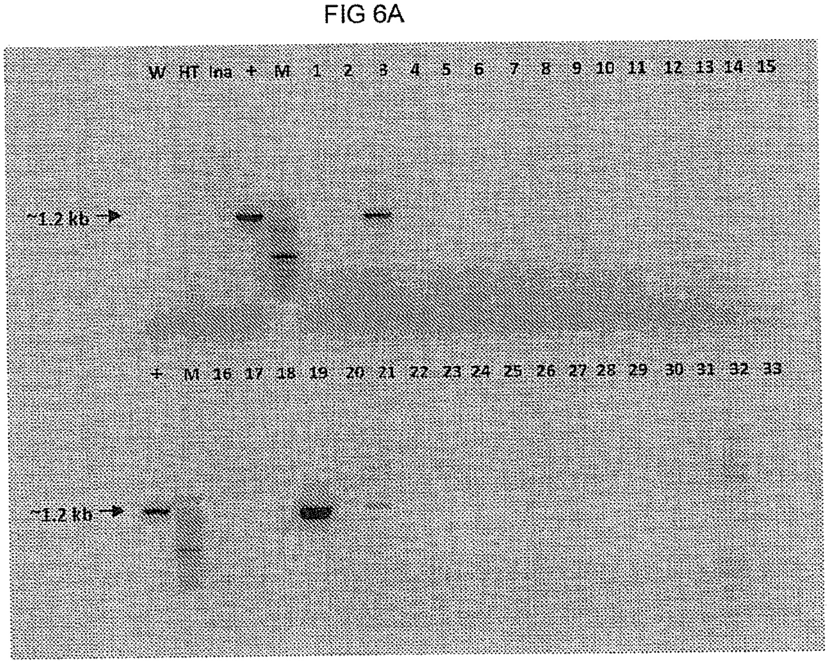
FIG. 6A shows the PCR results of screening for attH4x and attP4x recombination events at L1 loci in the HT1080 clones. PCR amplifications of the expected size (~1200 bp; for the attL site generated through recombination between attH4x and attP4x) were detected for the HT1080 clones 3, 19 and 21. W, no DNA template control; HT, negative control (genomic DNA from the parental HT1080 cells); In a, genomic DNA from puromycin resistant colonies obtained through co-transfection of pPGKssPuro-attP4x and pCMVssKZ-Inactivie Int (plasmid expressing integrase with an inactivating mutation wherein the amino acid residue tyrosine at sequence position 342 is replaced by the amino acid alanine); +, positive control (genomic DNA from HT1080 clone having an attH4x×attP4x integration event in L1 element); M, 100 bp DNA ladder; 1 to 33, genomic DNA from puromycin resistant HT1080 colonies obtained through co-transfection of pPGKssPuro-attP4x and pCMVssKZ-IntC3-CNLS.

FIG. 6A depicts the PCR results of screening for attH4x and attP4x recombination events at the L1 loci in the HT1080 clones. PCR amplifications of the expected size (~1200 bp; for the attL site generated through recombination between attH4x and attP4x) were detected for the HT1080 clones 3, 19 and 21. FIG. 6B shows the nucleotide sequence of attL site generated through recombination between the attH4x and attP4x in the HT1080 clones 3 and 19.

Applications

The improved in vitro recombination by using the integrase variants of the present invention and the attH/attPH and attH4X/attP4X substrate pairs indicates that the integrase variants described herein may be a useful reagent tool for biotechnology applications such as recombination-based cloning applications.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A lambda integrase mutant comprising the amino acid sequence of SEQ ID NO: 1, except for amino acid mutations at positions corresponding to residues 336, 319 and 43 of the amino acid sequence of SEQ ID NO: 1, wherein the isoleucine corresponding to position 43 of SEQ ID NO: 1 is replaced by an aromatic amino acid, glutamate corresponding to position 319 of SEQ ID NO: 1 is replaced by glycine and wherein the aspartate corresponding to position 336 of SEQ ID NO: 1 is replaced by a hydrophobic amino acid, and wherein the lambda integrase mutant has integrase activity.

2. The lambda integrase mutant according to claim 1, wherein the isoleucine corresponding to position 43 of SEQ ID NO: 1 is replaced by an aromatic amino acid selected from the group consisting of phenylalanine, tyrosine and tryptophan, optionally wherein the aspartate corresponding to position 336 of SEQ ID NO: 1 is replaced by a hydrophobic amino acid selected from the group consisting of isoleucine, leucine and valine.

3. The lambda integrase mutant according to claim 1, wherein the lambda integrase mutant comprises the amino acid sequence of SEQ ID NO: 3.

4. A nucleic acid molecule comprising a nucleotide sequence encoding the lambda integrase mutant of claim 1.

5. The nucleic acid molecule according to claim 4, wherein the nucleic acid molecule is operably linked to a regulatory sequence to permit expression of the nucleic acid molecule, optionally wherein the regulatory sequence comprises a promoter sequence, and optionally wherein the nucleic acid molecule is located in a vector.

6. An isolated host cell comprising the nucleic acid molecule according to claim 4.

7. A method of recombining a nucleic acid of interest into a target nucleic acid, the method comprising contacting a targeting nucleic acid comprising the nucleic acid of interest with the target nucleic acid in the presence of the lambda integrase mutant of claim 1 to thereby recombine the nucleic acid of interest into the target nucleic acid.

8. The method according to claim 7, wherein the target nucleic acid comprises DNA, optionally wherein the target nucleic acid comprises genomic DNA, optionally wherein the target nucleic acid comprises a sequence selected from the group consisting of an attH sequence comprising the nucleotide sequence of SEQ ID NO: 7 and an attH4X sequence comprising the nucleotide sequence of SEQ ID NO: 31, optionally wherein the targeting nucleic acid is a vector, optionally wherein the targeting nucleic acid comprises a sequence selected from the group consisting of an attPH sequence comprising the nucleotide sequence of SEQ ID NO: 8 and an attP4X sequence comprising the nucleotide sequence of SEQ ID NO: 9.

9. The method according to claim 7, wherein the sequence specific recombination is performed in the presence of one or more cofactors, optionally wherein the cofactors is selected from the group consisting of excisionase (XIS), factor for inversion simulation (FIS) and integration host factor (IHF).

10. The method according to claim 8, wherein the genomic DNA is comprised in an isolated cell.

11. A sequence specific recombination kit comprising:

a. a targeting nucleic acid into which a nucleic acid of interest can be inserted, and b. the lambda integrase mutant of claim 1 or a nucleic acid molecule comprising a nucleotide sequence encoding the lambda integrase mutant of claim 1.

12. The kit according to claim 11, further comprising at least one reagent for inserting said nucleic acid of interest into said targeting nucleic acid, optionally wherein said targeting nucleic acid comprises a sequence selected from the group consisting of an attPH sequence comprising the nucleotide sequence of SEQ ID NO: 8 and an attP4X sequence comprising the nucleotide sequence of SEQ ID NO: 9, optionally wherein said target nucleic acid comprises a sequence selected from the group consisting of an attH sequence comprising the nucleotide sequence of SEQ ID NO: 7 and an attH4X sequence comprising the nucleotide sequence of SEQ ID NO: 31.

13. The kit according to claim 11, further comprising buffer(s) and/or instructions for recombining said nucleic acid of interest with a given target nucleic acid, optionally further comprising at least one reagent for determining a successful sequence specific recombination event, optionally wherein said reagent is a primer pair.

* * * * *